US012186342B2

(12) United States Patent
Gaensler

(10) Patent No.: US 12,186,342 B2
(45) Date of Patent: Jan. 7, 2025

(54) AUTOLOGOUS IRRADIATED WHOLE CELL TUMOR VACCINES LENTIVIRALLY ENGINEERED TO EXPRESS CD80, IL-15 AND IL-15 RECEPTOR ALPHA

(71) Applicant: The Regents of the University of California, Oakland, CA (US)

(72) Inventor: Karin Gaensler, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 462 days.

(21) Appl. No.: 16/335,653

(22) PCT Filed: Sep. 25, 2017

(86) PCT No.: PCT/US2017/053313
§ 371 (c)(1),
(2) Date: Mar. 21, 2019

(87) PCT Pub. No.: WO2018/058067
PCT Pub. Date: Mar. 29, 2018

(65) Prior Publication Data
US 2020/0179447 A1    Jun. 11, 2020

Related U.S. Application Data

(60) Provisional application No. 62/398,980, filed on Sep. 23, 2016.

(51) Int. Cl.
| | |
|---|---|
| *A61K 35/13* | (2015.01) |
| *A61K 35/15* | (2015.01) |
| *A61K 38/20* | (2006.01) |
| *A61K 39/00* | (2006.01) |
| *A61P 35/02* | (2006.01) |
| *C12N 5/09* | (2010.01) |
| *C12N 5/10* | (2006.01) |
| *C12N 13/00* | (2006.01) |

(52) U.S. Cl.
CPC .......... *A61K 35/13* (2013.01); *A61K 38/2086* (2013.01); *A61K 39/0011* (2013.01); *A61P 35/02* (2018.01); *C12N 5/0693* (2013.01); *C12N 5/0694* (2013.01); *C12N 5/10* (2013.01); *A61K 35/15* (2013.01); *A61K 2039/5152* (2013.01); *A61K 2039/5156* (2013.01); *A61K 2039/804* (2018.08); *C12N 13/00* (2013.01); *C12N 2501/2315* (2013.01)

(58) Field of Classification Search
CPC .......... A61K 35/13; A61K 38/2086; A61K 2039/5156; A61K 2039/5152; A61P 35/02; C12N 5/0694; C12N 5/10; C12N 5/0693
USPC ......... 424/93.21; 512/19.6; 435/372.2, 320.1
See application file for complete search history.

(56) References Cited

U.S. PATENT DOCUMENTS

| | | | |
|---|---|---|---|
| 9,278,128 B2 | 3/2016 | Weiner et al. | |
| 2002/0018767 A1 | 2/2002 | Lee et al. | |
| 2006/0165668 A1 | 7/2006 | Liu et al. | |
| 2007/0160578 A1 | 7/2007 | Waldmann et al. | |
| 2014/0205560 A1 | 7/2014 | Wong et al. | |
| 2016/0102128 A1* | 4/2016 | Felber ................ | C07K 14/7155 435/365.1 |
| 2017/0020963 A1* | 1/2017 | Qu .......................... | A61P 25/00 |

OTHER PUBLICATIONS

Chan et al. (2005) Mol. Ther., vol. 11(1), 120-131.*
Morris et al. (2014) Gene Therapy, vol. 21, 393-401.*
Klebanoff et al. (2004) PNAS, vol. 101(7), 1969-1974.*
Dunussi-joannopoulos et al. (2001) Leukemia and Lymphoma, vol. 41(5-6), 482-492.*
Ingram et al. (2009) Brit. J. Haematol., vol. 145, 749-760.*
Wen et al. (2001) Cancer Gene Therapy, vol. 8(5), 361-370.*
Anderson, D.M. et al. (Dec. 15, 1995). "Functional characterization of the human interleukin-15 receptor alpha chain and close linkage of IL15RA and IL2RA genes," *J Biol Chem* 270(50):29862-29869.
Bergamaschi, C. et al. (Feb. 15, 2008, e-published Nov. 30, 2007). "Intracellular interaction of interleukin-15 with its receptor alpha during production leads to mutual stabilization and increased bioactivity," *J Biol Chem* 283(7):4189-4199.
Bergamaschi, C. et al. (Sep. 1, 2009). "Secretion and biological activity of short signal peptide IL-15 is chaperoned by IL-15 receptor alpha in vivo," *J Immunol* 183(5):3064-3072.
Bergamaschi, C. et al. (Jul. 5, 2012, Apr. 10, 2012). "Circulating IL-15 exists as heterodimeric complex with soluble IL-15Rα in human and mouse serum," *Blood* 120(1):e1-8.
Berger, C. et al. (Mar. 15, 2006, e-published Nov. 10, 2005). "Analysis of transgene-specific immune responses that limit the in vivo persistence of adoptively transferred HSV-TK-modified donor T cells after allogeneic hematopoietic cell transplantation," *Blood* 107(6):2294-2302.
Bessard, A. et al. (Sep. 2009, e-published Sep. 1, 2009). "High antitumor activity of RLI, an interleukin-15 (IL-15)-IL-15 receptor alpha fusion protein, in metastatic melanoma and colorectal cancer," *Mol Cancer Ther* 8(9):2736-2745.
Borrello, I.M. et al. (Aug. 7, 2009, e-published Jun. 25, 2009). "Granulocyte-macrophage colony-stimulating factor (GM-CSF)-secreting cellular immunotherapy in combination with autologous stem cell transplantation (ASCT) as postremission therapy for acute myeloid leukemia (AML)," *Blood* 114(9):1736-1745.
Boyer, M.W. et al. (May 1, 1997). "The role of B7 costimulation by murine acute myeloid leukemia in the generation and function of a CD8+ T-cell line with potent in vivo graft-versus-leukemia properties," *Blood* 89(9):3477-3485.
Carlyle, J.R. et al. (Jun. 15, 2006). "Molecular and genetic basis for strain-dependent NK1.1 alloreactivity of mouse NK cells," *J Immunol* 176(12):7511-7524.

(Continued)

Primary Examiner — Anne Marie S Wehbe
(74) Attorney, Agent, or Firm — MINTZ, LEVIN, COHN, FERRIS, GLOVSKY & POPEO, P.C.

(57) ABSTRACT

Provided herein, inter alia, are cell media compositions and whole cell vaccines comprising recombinant cells expressing IL-15, IL-15Rα, and CD80 capable of treating and preventing relapse in individuals diagnosed with or thought to have leukemia as well as methods for using the same.

19 Claims, 23 Drawing Sheets

Specification includes a Sequence Listing.

(56) References Cited

OTHER PUBLICATIONS

Chan, L. et al. (Jan. 2005). "IL-2/B7.1 (CD80) fusagene transduction of AML blasts by a self-inactivating lentiviral vector stimulates T cell responses in vitro: a strategy to generate whole cell vaccines for AML," *Mol Ther* 11(1):120-131.

Chertova, E. et al. (Jun. 21, 2013, e-published May 6, 2013). "Characterization and favorable in vivo properties of heterodimeric soluble IL-15·IL-15Rα cytokine compared to IL-15 monomer," *J Biol Chem* 18093-18103.

Ciernik, I.F. et al. (Oct. 1, 1999). "Ionizing radiation enhances immunogenicity of cells expressing a tumor-specific T-cell epitope," *Int J Radiant Oncol Biol Phys* 45(3):735-741.

Comes, A. et al. (Jul. 2002). "IFN-gamma-independent synergistic effects of IL-12 and IL-15 induce anti-tumor immune responses in syngeneic mice," *Eur J Immunol* 32(7):1914-1923.

Cook, G.J. et al. (Jun. 2013). "Animal models of leukemia: any closer to the real thing?" *Cancer Metastasis Rev* 32(1-2):63-76.

Daley, G.Q. et al. (Feb. 16, 1990). "Induction of chronic myelogenous leukemia in mice by the P210bcr/abl gene of the Philadelphia chromosome," *Science* 247(4944):824-830.

Dicarlo, E. et al. (Sep. 15, 2000). "The combined action of IL-15 and IL-12 gene transfer can induce tumor cell rejection without T and NK cell involvement," *J Immunol* 165(6):3111-3118.

Distasi, A. et al. (Feb. 4, 2015). "Review of the Results of WT1 Peptide Vaccination Strategies for Myelodysplastic Syndromes and Acute Myeloid Leukemia from Nine Different Studies," *Front Immunol* 6:36, 6 pages.

Dombret, H. et al. (Jan. 7, 2016, e-published Dec. 10, 2015). "An update of current treatments for adult acute myeloid leukemia," *Blood* 127(1):53-61.

Donnelly, M.L. et al. (May 2001). "The 'cleavage' activities of foot-and-mouth disease virus 2A site-directed mutants and naturally occurring '2A-like' sequences," *J Gen Virol* 82(Pt 5):1027-1041.

Dranoff, G. et al. (Apr. 15, 1993). "Vaccination with irradiated tumor cells engineered to secrete murine granulocyte-macrophage colony-stimulating factor stimulates potent, specific, and long-lasting anti-tumor immunity," *PNAS USA* 90(8):3539-3543.

Dubois, S. et al. (Nov. 2002). "IL-15Rα recycles and presents IL-15 In trans to neighboring cells," *Immunity* 17(5):537-547.

Falahati, R. et al. (Nov. 2012, e-published Aug. 7, 2012). "Chemoselection of allogeneic HSC after murine neonatal transplantation without myeloablation or post-transplant immunosuppression," *Mol Ther* 20(11):2180-2189.

Gillgrass, A. et al. (Dec. 15, 2014, e-published Oct. 29, 2014). "The absence or overexpression of IL-15 drastically alters breast cancer metastasis via effects on NK cells, CD4 T cells, and macrophages," *J Immunol* 193(12):6184-6191.

Giorda, R. et al. (Sep. 15, 1992). "Genomic structure and strain-specific expression of the natural killer cell receptor NKR-P1," *J Immunol* 149(6):1957-1963.

Gravekamp, C. et al. (Aug. 2011, e-published Jul. 18, 2011). "The impact of aging on cancer vaccination," *Curr Opin Immunol* 23(4):555-560.

Grosso, D.A. et al. (Aug. 15, 2015, e-published Jun. 10, 2015). "Immunotherapy in acute myeloid leukemia," *Cancer* 121(16):2689-2704.

Hadrup, S.R. et al. (Feb. 15, 2006). "Longitudinal studies of clonally expanded CD8 T cells reveal a repertoire shrinkage predicting mortality and an increased number of dysfunctional cytomegalovirus-specific T cells in the very elderly," *J Immunol* 176(4):2645-2653.

Hardwick, N. et al. (Mar. 2010, e-published Aug. 27, 2009). "Lytic activity against primary AML cells is stimulated in vitro by an autologous whole cell vaccine expressing IL-2 and CD80," *Cancer Immunol Immunother* 59(33):379-388.

Hasan, A.N et al. (Nov. 2016, e-published Aug. 31, 2016). "Soluble and membrane-bound interleukin (IL)-15 Rα/IL-15 complexes mediate proliferation of high-avidity central memory CD8+ T cells for adoptive immunotherapy of cancer and infections," *Clin Exp Immunol* 186(2):249-265.

Hong, E. et al. (Apr. 22, 2016, e-published Dec. 30, 2015). "Configuration-dependent Presentation of Multivalent IL-15:IL-15Rα Enhances the Antigen-specific T Cell Response and Anti-tumor Immunity," *J Biol Chem* 291(17):8931-8950.

Hu, J. et al. (Jul. 1, 2014, e-published Jun. 2, 2014). "Lysophosphatidic acid receptor 5 inhibits B cell antigen receptor signaling and antibody response," *J Immunol* 193(1):85-95.

Ingram, W. et al. (Jun. 2009, e-published Apr. 20, 2009). "Human CD80/IL2 lentivirus-transduced acute myeloid leukaemia (AML) cells promote natural killer (NK) cell activation and cytolytic activity: implications for a phase I clinical study," *Br J Haematol* 145(6):749-760.

International Search Report mailed on Dec. 11, 2017 for PCT Application No. PCT/US2017/053313, Sep. 25, 2017, 3 pages.

Jalah, R. et al. (Dec. 2007). "Efficient systemic expression of bioactive IL-15 in mice upon delivery of optimized DNA expression plasmids," *DNA Cell Biol* 26(12):827-840.

Kim, J.H. et al. (2011, e-published Apr. 29, 2011). "High cleavage efficiency of a 2A peptide derived from porcine teschovirus-1 in human cell lines, zebrafish and mice," *PLoS One* 6(4):e18556.

Kishida, T. et al. (Nov. 2003). "Electrochemo-gene therapy of cancer: intratumoral delivery of interleukin-12 gene and bleomycin synergistically induced therapeutic immunity and suppressed subcutaneous and metastatic melanomas in mice," *Mol Ther* 8(5):738-745.

Kowalczyk, A. et al. (Sep. 2007). "Induction of protective immune responses against NXS2 neuroblastoma challenge in mice by immunotherapy with GD2 mimotope vaccine and IL-15 and IL-21 gene delivery," *Cancer Immunol Immunother* 56(9):1443-1458.

Koya, R.C. et al. (Sep. 2002 _. "Transduction of acute myeloid leukemia cells with third generation self-inactivating lentiviral vectors expressing CD80 and GM-CSF: effects on proliferation, differentiation, and stimulation of allogeneic and autologous antileukemia immune responses," *Leukemia* 16(9):1645-1654.

Matulonis, U. et al. (Oct. 1993). "Interleukin-3 and p210 BCR/ABL activate both unique and overlapping pathways of signal transduction in a factor-dependent myeloid cell line," *Exp Hematol* 21(11):1460-1466.

McGavin, J.K. et al. (2001). "Ganciclovir: an update of its use in the prevention of cytomegalovirus infection and disease in transplant recipients," *Drugs* 61(8):1153-1183.

Mehta, R.S. et al. (Feb-Mar. 2016). "Generating Peripheral Blood Derived Lymphocytes Reacting Against Autologous Primary AML Blasts," *J Immuonother* 39(2):71-80.

Mocchegiani, E. et al. (Aug. 2004). "NK and NKT cell functions in immunosenescence," *Aging Cell* 3(4):177-184.

Mortier, E. et al. (May 12, 2008, e-published May 5, 2008). "IL-15Rachaperones IL-15 to stable dendritic cell membrane complexes that activate NK cells via trans presentation," *J Exp Med* 205(5):1213-1225.

Nishikado, H. et al. (May 15, 2011 e-published Apr. 13, 2011). "NK cell-depleting anti-asialo GM1 antibody exhibits a lethal off-target effect on basophils in vivo," *J Immunol* 186(10):5766-5771.

Plebanski, M. et al. (Jun. 2010). "Methods to measure T-cell responses," *Expert Rev Vaccines* 9(6):595-600.

Posnett, D.M. et al. (Feb. 1, 1994). "Clonal populations of T cells in normal elderly humans: the T cell equivalent to benign monoclonal gammapathy," *J Exp Med* 179(2):609- 618.

Rashidi, A. et al. (2016, e-published Feb. 6, 2016). "Antigen-specific immunotherapy for acute myeloid leukemia: where are we now, and where do we go from here?" *Exper Rev Hematol* 9(4):335-350.

Rivas, C. et al. (May 2001). "BCR-ABL-expressing cells transduced with the HSV-tk gene die by apoptosis upon treatment with ganciclovir," *Mol Ther* 3(5 Pt 1):642-652.

Romano, E. et al. (May 31, 2012, e-published Apr. 17, 2012). "Human Langerhans cells use an IL-15R-α/IL-15/pSTAT5-dependent mechanism to break T-cell tolerance against the self-differentiation tumor antigen WT1," *Blood* 119(22):5182-5190.

(56) References Cited

OTHER PUBLICATIONS

Rosati, M. et al. (Sep. 19, 2008, e-published Apr. 21, 2008). "Increased immune responses in rhesus macaques by DNA vaccination combined with electroporation," *Vaccine* 26(40):5223-5229.
Sandau, M.M. et al. (Dec. 1, 2004). "Cutting edge: transpresentation of IL-15 by bone marrow-derived cells necessitates expression of IL-15 and IL-15R α by the same cells," *J Immunol* 173(11):6537-6541.
Sasine, J.P. et al. (Jan. 2015, e-published Jul. 16, 2014). "Emerging strategies for high-risk and relapsed/refractory acute myeloid leukemia: novel agents and approaches currently in clinical trials," Blood Rev 29(1):1-9.
Slifka, M.K. et al. (Feb. 15, 2000). NK markers are expressed on a high percentage of virus-specific CD8+ and CD4+ T cells, *J Immunol* 164(4):2009-2015.
Stitz, L. et al. (Jun. 5, 1986). "Effect of rabbit anti-asialo GM1 treatment in vivo or with anti-asialo GM1 plus complement in vitro on cytotoxic T cell activities," *J Immunol* 136(12):4674-4680.
Stoklasek, T.A. et al. (Nov. 1, 2006). "Combined IL-15/IL-15Ralpha immunotherapy maximizes IL-15 activity in vivo," *J Immunol* 177(9):6072-6080.
Sun, H. et al. (February-Mar. 2016, e-published Jan. 8, 2016). "IL-15/sIL-15Rα gene transfer suppresses Lewis lung cancer growth in the lungs, liver and kidneys," *Cancer Gene Ther* 23(2-3):54-60.
Sweeney, C.L. et al. (Mar. 2002). "Methotrexate exacerbates tumor progression in a murine model of chronic myeloid leukemia," *J Pharmacol Exp Ther* 300(30:1075-1084.
Sweeney, C.L. et al. (Mar. 15, 2003). "Trimetrexate inhibits progression of the murine 32Dp210 model of chronic myeloid leukemia in animals expressing drug-resistant dihydrofolate reductase," *Cancer Res* 63(6):1304-1310.
Teague, R.M. et al. (Aug. 27, 2013). "Immune evasion in acute myeloid leukemia: current concepts and future directions," *J Immunother Cancer* 1(13).
Vallera, D.A. et al. (Sep. 1999). "Targeting myeloid leukemia with a $DT_{(390)}$-mIL-3 fusion immunotoxin: ex vivo and in vivo studies in mice," *Protein Eng* 12(9):779-785.

Vandenbergh, J. et al. (Dec. 29, 2015). "Transpresentation of interleukin-15 by IL-15/IL-15Rα mRNA-engineered human dendritic cells boosts antitumoral natural killer cell activity," *Oncotarget* 6(42):44123-44133.
Varma, T.K. et al. (Sep. 2001). "Cellular mechanisms that cause suppressed gamma interferon secretion in endotoxin-tolerant mice," *Infect Immun* 69(9):5249-5263.
Waldmann, T.A. et al. (May 5, 2011, e-published Mar. 8, 2011). "Safety (toxicity), pharmacokinetics, immunogenicity, and impact on elements of the normal immune system of recombinant human IL-15 in rhesus macaques," *Blood* 117(18):4787-4795.
Waldmann, T.A. et al. (Mar. 2015). "The shared and contrasting roles of IL2 and IL15 in the life and death of normal and neoplastic lymphocytes: implications for cancer therapy," Cancer Immunol Res 3(3):219-227.
Written Opinion mailed on Dec. 11, 2017 for PCT Application No. PCT/US2017/053313, Sep. 25, 2017, 6 pages.
Xu, W. et al. (May 15, 2013, e-published May 3, 2013). "Efficacy and mechanism-of-action of a novel superagonist interleukin-15: interleukin-15 receptor αSu/Fc fusion complex in syngeneic murine models of multiple myeloma," Cancer Res 73(10):3075-3086.
Zhang, M. et al. (Jun. 15, 2012, e-published May 16, 2012). "Augmented IL-15Rα expression by CD40 activation is critical in synergistic CD8 T cell-mediated antitumor activity of anti-CD40 antibody with IL-15 in TRAMP-C2 tumors in mice," *J Immunol* 188(12):6156-6164.
Brentjens, R.J. et al. (Mar. 2003, e-published Feb. 10, 2003). "Eradication of systemic B-cell tumors by genetically targeted human T lymphocytes co-stimulated by CD80 and interleukin-15," *Nat Med* 9(3):279-286.
Extended European Search Report mailed on May 29, 2020, for EP Patent Application No. 17854094.4, 10 pages.
Hasan, A.N. et al. (Aug. 15, 2009, e-published Jul. 27, 2009). "A panel of artificial APCs expressing prevalent HLA alleles permits generation of cytotoxic T cells specific for both dominant and subdominant viral epitopes for adoptive therapy," *J Immunol* 183(4):2837-2850.

\* cited by examiner

SEQUENCE LISTING

```
<160> NUMBER OF SEQ ID NOS: 6

<210> SEQ ID NO 1
<211> LENGTH: 162
<212> TYPE: PRT
<213> ORGANISM: Mus musculus

<400> SEQUENCE: 1

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
```

```
                    85                  90                  95
Val Ile Leu His Glu Tyr Ser Asn Met Thr Leu Asn Glu Thr Val Arg
                100                 105                 110

Asn Val Leu Tyr Leu Ala Asn Ser Thr Leu Ser Ser Asn Lys Asn Val
            115                 120                 125

Ala Glu Ser Gly Cys Lys Glu Cys Glu Glu Leu Glu Glu Lys Thr Phe
        130                 135                 140

Thr Glu Phe Leu Gln Ser Phe Ile Arg Ile Val Gln Met Phe Ile Asn
145                 150                 155                 160

Thr Ser

<210> SEQ ID NO 2
<211> LENGTH: 162
<212> TYPE: PRT
<213> ORGANISM: Homo sapiens

<400> SEQUENCE: 2

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser

<210> SEQ ID NO 3
<211> LENGTH: 267
<212> TYPE: PRT
<213> ORGANISM: Homo sapiens

<400> SEQUENCE: 3

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80
```

```
Thr Asn Val Ala His Trp Thr Thr Pro Ser Leu Lys Cys Ile Arg Asp
                 85                  90                  95

Pro Ala Leu Val His Gln Arg Pro Ala Pro Ser Thr Val Thr Thr
            100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
            195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265
```

```
<210> SEQ ID NO 4
<211> LENGTH: 263
<212> TYPE: PRT
<213> ORGANISM: Mus musculus

<400> SEQUENCE: 4

Met Ala Ser Pro Gln Leu Arg Gly Tyr Gly Val Gln Ala Ile Pro Val
1               5                   10                  15

Leu Leu Leu Leu Leu Leu Leu Leu Leu Pro Leu Arg Val Thr Pro
            20                  25                  30

Gly Thr Thr Cys Pro Pro Val Ser Ile Glu His Ala Asp Ile Arg
        35                  40                  45

Val Lys Asn Tyr Ser Val Asn Ser Arg Glu Arg Tyr Val Cys Asn Ser
            50                  55                  60

Gly Phe Lys Arg Lys Ala Gly Thr Ser Thr Leu Ile Glu Cys Val Ile
65                  70                  75                  80

Asn Lys Asn Thr Asn Val Ala His Trp Thr Thr Pro Ser Leu Lys Cys
                85                  90                  95

Ile Arg Asp Pro Ser Leu Ala His Tyr Ser Pro Val Pro Thr Val Val
            100                 105                 110

Thr Pro Lys Val Thr Ser Gln Pro Glu Ser Pro Ser Pro Ser Ala Lys
            115                 120                 125

Glu Pro Glu Ala Phe Ser Pro Lys Ser Asp Thr Ala Met Thr Thr Glu
130                 135                 140

Thr Ala Ile Met Pro Gly Ser Arg Leu Thr Pro Ser Gln Thr Thr Ser
145                 150                 155                 160

Ala Gly Thr Thr Gly Thr Gly Ser His Lys Ser Ser Arg Ala Pro Ser
                165                 170                 175

Leu Ala Ala Thr Met Thr Leu Glu Pro Thr Ala Ser Thr Ser Leu Arg
            180                 185                 190
```

```
Ile Thr Glu Ile Ser Pro His Ser Lys Met Thr Lys Val Ala Ile
            195                 200                 205

Ser Thr Ser Val Leu Leu Val Gly Ala Gly Val Val Met Ala Phe Leu
    210                 215                 220

Ala Trp Tyr Ile Lys Ser Arg Gln Pro Ser Gln Pro Cys Arg Val Glu
225                 230                 235                 240

Val Glu Thr Met Glu Thr Val Pro Met Thr Val Arg Ala Ser Ser Lys
                245                 250                 255

Glu Asp Glu Asp Thr Gly Ala
                260

<210> SEQ ID NO 5
<211> LENGTH: 288
<212> TYPE: PRT
<213> ORGANISM: Homo sapiens

<400> SEQUENCE: 5

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

```
<210> SEQ ID NO 6
<211> LENGTH: 306
<212> TYPE: PRT
<213> ORGANISM: Mus musculus

<400> SEQUENCE: 6

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305
```

AUTOLOGOUS IRRADIATED WHOLE CELL TUMOR VACCINES LENTIVIRALLY ENGINEERED TO EXPRESS CD80, IL-15 AND IL-15 RECEPTOR ALPHA

CROSS-REFERENCE TO RELATED APPLICATIONS

This application is a U.S. National Phase Application of PCT International Application No. PCT/US2017/053313, filed on Sep. 25, 2017, designating the United States of America, which is an International Application of and claims the benefit of priority to U.S. Provisional Patent Application No. 62/398,980, filed on Sep. 23, 2016. The disclosures of the above-referenced applications are hereby expressly incorporated by reference in their entireties.

STATEMENT AS TO RIGHTS TO INVENTIONS MADE UNDER FEDERALLY SPONSORED RESEARCH AND DEVELOPMENT

This invention was made with government support under grant nos. R21 CA177284 and TR000004, awarded by The National Institutes of Health. The government has certain rights in the invention.

SEQUENCE LISTING STATEMENT

The present application contains a Sequence Listing, which is being submitted via EFS-Web on even date herewith. The Sequence Listing is submitted in a file entitled "Sequence Listing_048536-588N01US.txt," which was created on Mar. 20, 2019, and is approximately 13 kb in size. This Sequence Listing is hereby incorporated by reference.

BACKGROUND OF THE INVENTION

Compelling evidence for the efficacy of immunotherapy in eliminating minimal residual disease (MRD) in acute myelogenous leukemia (AML) is provided by the superior outcomes of allogeneic hematopoietic stem cell transplants (HSCT) and donor leukocyte infusion (DLI) due to graft vs leukemia (GVL) effects. However, older patients are often ineligible for allo-HSCT, due to co-morbidities or lack of a donor, and have dismal outcomes. Although 40-50% of patients achieve remission, most relapse from residual disease persisting after chemotherapy. There is a need in the field for compositions and methods that combine expression of a costimulatory molecule required for optimal T cell activation and leukemia-specific cytolytic effects with the properties of IL-15/IL-15Rα immune stimulation of both natural killer cells in the innate immune system and long-lived effector memory T cells in the context of the patient's unique profile of both common and undefined tumor associated antigens.

Methods and compositions of the present invention provide a personalized immunotherapeutic strategy to increase progression free survival in this patient population for whom there are no safe and effective treatment options.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF SUMMARY OF THE INVENTION

Provided herein, inter alia, are cell media compositions and methods for the stimulation of an immune response and in particular the treatment of acute myelogenous leukemia.

Accordingly, in some aspects, provided herein is a cell media composition comprising (1) recombinant cells comprising IL-15, IL15-R, and CD80 wherein the cells are capable of expressing IL-15, IL15-R, and CD80 and (2) IL-15 in the media. In some embodiments, comprising about 150-400 ng/mL IL-15 in the media. In some embodiments of any of the embodiments disclosed herein, the recombinant cell is a cancer cell. In some embodiments of any of the embodiments disclosed herein, the recombinant cell is derived from an individual diagnosed with or thought to have cancer. In some embodiments, the individual is in remission for a cancer. In some embodiments, the cancer is a leukemia. In some embodiments, the leukemia is acute myeloid leukemia. In some embodiments of any of the embodiments disclosed herein, the individual is about 60 years of age or older. In some embodiments of any of the embodiments disclosed herein, the composition is irradiated. In some embodiments of any of the embodiments disclosed herein, the recombinant cells are created by transduction with a vector comprising mIL-15/IL-15Rα, and CD80. In some embodiments, the vector is a lentiviral vector. In some embodiments of any of the embodiments disclosed herein, the vector is a tri-cistronic vector. In some embodiments of any of the embodiments disclosed herein, the composition is sterilely formulated for administration into an individual. In some embodiments of any of the embodiments disclosed herein, the individual is a human.

In other aspects, provided herein is a method of stimulating an immune response in individuals with AML in remission with persistent minimal residual disease (MRD), comprising administering an effective amount of a composition comprising recombinant cells comprising IL-15, IL15-R, and CD80 wherein the cells are capable of expressing IL-15, IL15-Ra, and CD80. In some embodiments, the cells are capable of expressing about 150-400 ng/mL IL-15 in the media. In some embodiments of any of the embodiments disclosed herein, the recombinant cells are autologous cells derived from the individual. In some embodiments of any of the embodiments disclosed herein, the individual is about 60 years of age or older. In some embodiments of any of the embodiments disclosed herein, the composition is irradiated. In some embodiments of any of the embodiments disclosed herein, the recombinant cells are created by transduction with a vector comprising mIL-15/IL-15Rα, and CD80. In some embodiments, the vector is a lentiviral vector. In some embodiments of any of the embodiments disclosed herein, the vector is a tri-cistronic vector. In some embodiments of any of the embodiments disclosed herein, the composition is sterilely formulated for administration into an individual. In some embodiments of any of the embodiments disclosed herein, the individual is a human. In some embodiments, the method stimulates the proliferation of one or more of CD3+CD8$^+$ T cells, CD3+CD4$^+$ T cells, memory CD8$^+$ T cells, NK cells, and NKT cells relative to the proliferation of one or more of these cells in individuals who have not been administered the composition. In some embodiments, the method stimulates the proliferation of CD3+CD8$^+$ T cells and/or CD3+CD4$^+$ T cells up to five fold relative to the proliferation of one or more of these cells in individuals who have not been administered the composition. In some embodiments of any of the embodiments disclosed herein, the method stimulates increased production of interferon gamma (IFNγ) relative to the production of IFNγ in individuals who have not been administered the composition. In some embodiments of any of the embodiments disclosed herein, the method prevents relapse of AML relative to the rate of relapse of AML in individuals who have not been administered the composition. In some embodiments of any of the embodiments disclosed herein, the method further comprises administering the composition or vaccine in combination with one or more anti-cancer therapies.

In further aspects, provided herein, is a method of increasing the population of one or more cell types selected from the group consisting of CD3+CD8+ T cells, CD3+CD4+ T cells, memory CD8+ T cells, NK cells, and NKT cells in individuals in need thereof comprising administering an effective amount of a composition comprising recombinant cells comprising IL-15, IL15-R, and CD80 wherein the cells are capable of expressing IL-15, IL15-R, and CD80. In some embodiments, the method stimulates the proliferation of CD3+CD8+ T cells and/or CD3+CD4+ T cells up to five fold relative to the proliferation of one or more of these cells in individuals who have not been administered the composition. In some embodiments of any of the embodiments disclosed herein, the method stimulates increased production of interferon gamma (IFNγ) relative to the production of IFNγ in individuals who have not been administered the composition. In some embodiments of any of the embodiments disclosed herein, the recombinant cells are autologous cells derived from the individual. In some embodiments of any of the embodiments disclosed herein, the recombinant cell is a cancer cell. In some embodiments, the cancer is a leukemia. In some embodiments, the leukemia is acute myeloid leukemia. In some embodiments of any of the embodiments disclosed herein, the individual is about 60 years of age or older. In some embodiments of any of the embodiments disclosed herein, the composition is irradiated. In some embodiments of any of the embodiments disclosed herein, the recombinant cells are created by transduction with a vector comprising mIL-15/IL-15Rα, and CD80. In some embodiments, the vector is a lentiviral vector. In some embodiments of any of the embodiments disclosed herein, the vector is a tri-cistronic vector. In some embodiments of any of the embodiments disclosed herein, the composition is sterilely formulated for administration into an individual. In some embodiments of any of the embodiments disclosed herein, the individual is a human. In some embodiments of any of the embodiments disclosed herein, the method further comprises administering the composition or vaccine in combination with one or more anti-cancer therapies.

In yet other aspects, provided herein is a method for treating acute myelogenous leukemia (AML) in an individual in need thereof, comprising administering a therapeutically effective amount of a whole cell vaccine comprising recombinant cells comprising IL-15, IL-15Rα and CD80 to the individual. In some embodiments, the recombinant cells are autologous cells derived from the individual. In some embodiments of any of the embodiments disclosed herein, the cells are irradiated. In some embodiments of any of the embodiments disclosed herein, the method stimulates the proliferation of CD3+CD8+ T cells and/or CD3+CD4+ T cells up to five fold relative to the proliferation of one or more of these cells in individuals who have not been administered the vaccine. In some embodiments of any of the embodiments disclosed herein, the method stimulates increased production of interferon gamma (IFNγ) relative to the production of IFNγ in individuals who have not been administered the vaccine. In some embodiments of any of the embodiments disclosed herein, the method results in increased progression free survival of the individual relative to the rate of progression free survival in individuals with AML who have not been administered the vaccine. In some embodiments of any of the embodiments disclosed herein, the individual is a human. In some embodiments of any of the embodiments disclosed herein, the method further comprises administering the composition or vaccine in combination with one or more anti-cancer therapies.

In another aspect, provided herein is a syringe comprising any of the vaccine or media compositions disclosed herein.

In still further aspects, provided herein is a catheter comprising any of the vaccine or media compositions disclosed herein.

In further aspects, provided herein, is a method of enhancing immune responses to a whole cell vaccine in individuals having or suspected of having AML comprising a administering composition comprising recombinant cells comprising IL-15, IL15-Ra and CD80.

In further aspects, provided herein, is a method of treating AML in remission with persistent minimal residual disease comprising administering to a patient in need thereof an effective amount of a composition comprising recombinant cells comprising IL-15, IL15-R, and CD80, wherein said cells are capable of expressing IL-15, IL15-R, and CD80 on the cell surface.

Each of the aspects and embodiments described herein are capable of being used together, unless excluded either explicitly or clearly from the context of the embodiment or aspect.

BRIEF DESCRIPTION OF THE DRAWINGS

(FIG. 8A) percent CD3+CD4+ T cells, (FIG. 8B) percent CD4+CD8+ T cells, (FIG. 8C) frequency of $CD44^{hi}$ CD3+CD4+ T cells, (FIG. 8D) frequency of $CD44^{hi}$ CD3+CD8+ T cells, (FIG. 8E) percent CD4+FoxP3+ T regulatory cells ($T_{REG}$), and (FIG. 8F) percent CD11b+Ly6G+ myeloid derived suppressor cells (MDSC). *$p<0.05$, $p<0.01$, *$p<0.001$; Error bars=S.E.M. Similar changes in the absolute numbers of these populations also observed (FIG. 8G-FIG. 8J).

FIG. 10A depicts levels of IL-15 secretion after lentiviral transduction of 293T cells. Murine IL-15 secretion was quantified by ELISA assays of tissue culture supernatants 48 hours after transfection. On the left are designations of lentiviral vectors generated for transduction studies. Asterisks denote vectors that were used to generate the final 32Dp210 vaccines. Lanes 1-5 depict IL-15 secretion detected as ng/ml as detected by ELISA. Bars represent the mean cytokine concentration±S.E.M. FIG. 10B depicts levels of IL-15 secretion after lentiviral transduction of 32Dp210 cells, with and without irradiation. 32Dp210 cells transduced with lentiviral vectors containing mIL-15/IL-15Rα, or CD80, or both IL-15/IL-15Rα and CD80, were expanded, and populations normalized to express similar levels of cell-surface IL-15Rα and/or CD80 purified by FACS. Levels of IL-15 in culture supernatants (ng/ml) were measured before (white bars) and 48 hours after irradiation with 40Gy (gray bars). 32Dp210, appearing in the top 2 lanes designates the untransduced parent cell line controls. Designations to the left of the graph indicate the genes (IL15, IL15Rα or CD80, or all three cassettes) contained in the lentiviral vector used to transduce the 32Dp210 cells analyzed. Levels of IL15 detected in cell culture medium are indicated (ng/ml) on the horizontal axis.

(FIG. 13A) Proliferation of CD3+CD8+ T cells, (FIG. 13B) Proliferation of CD3+CD4+ T cells. Bar graphs to the right of the flow plots depict the mean percentage of dividing cells from triplicate wells+S.E.M. 32Dp210 indicates untransduced parental cell line. The lentivirally transduced gene, or genes, expressed by each of the transduced 32Dp210 lines are indicated below the bar graphs along the horizontal axis. (FIG. 14A) Proliferation of CD3+CD8+ T cells, (FIG. 14B) Proliferation of CD3+CD4+ T cells. Bar graphs to the right depict the mean percentage of dividing cells in triplicate wells±S.E.M. Transgenes expressed by each cell line are indicated along the x axis.

(FIG. 15A) Cytolytic activity of splenocytes at different effector to 32Dp210 target cell ratios. CellTrace DDAO-SE labeled splenocytes and $1\times10^5$ 32Dp210 target cells were co-cultured at different ratios (1:1, white bars, 5:1, gray bars 10:1, black bars) for 48 hours. On the horizontal axis: Naïve: indicates uninjected C3H mice, 32Dp210: vaccinated with the parent 32Dp210 cell line; IL-15/IL-15Rα, CD80, IL-15/IL-15Rα-CD80: depict assays with splenocytes from C3H mice treated with lentivirally transduced 32Dp210 vaccines expressing the indicated transgenes. The mean percentage of apoptotic cells, as defined by detection of activated caspase 3 by antibody staining is depicted on the Y axis, ±S.E.M. (FIG. 15B) Elispot assay of IFNγ expression by splenocytes from vaccinated mice. Splenocytes from unvaccinated mice (Naïve), or from mice vaccinated with irradiated parent cells 32Dp210 cells, or with engineered 32Dp210 cells expressing each of the transgene cassettes indicated on the horizontal axis below the bar graphs, were co-cultured with irradiated 32Dp210 cells and the frequency of IFNγ positive cells quantified. The mean number of spots per well per 3×10$^5$ cells in triplicate samples is depicted on the Y axis+S.E.M.

(FIG. 16A) Comparison of overall survival of mice with 32Dp210 leukemia after serial vaccination: Mice were inoculated with 32Dp210 leukemia and vaccination was initiated three days later as depicted in the schema at the top of the Figure. Experimental groups included mice inoculated with tumor with no further treatment (no vaccine, filled black circles, n=15), and mice vaccinated with parental 32Dp210 cells (open circles, n=15), 32Dp210-IL-15/IL-15Rα (filled black squares, n=15), 32Dp210-CD80 (open squares, n=15), or 32Dp210-IL-15/IL-15RαCD80 (filled triangles, n=25). Percent survival is depicted on the y axis, and duration of survival (days), beginning on day 0 with tumor inoculation, is shown on the x axis. Data represents the results of 3 independent experiments. (FIG. 16B) Effects of in vivo, antibody-mediated immune subset depletion on overall survival after vaccination of leukemic mice. After tumor inoculation on day 0, mice underwent three weekly vaccinations with 32Dp210-IL-15/IL-15Rα-CD80. Filled triangles depict vaccination without antibody depletion. Open Circles depict unvaccinated control mice inoculated with 32Dp210 leukemia. Antibody-mediated in vivo depletion of CD8+ cells (filled black circles, n=10), CD4+ cells (open squares, n=5), and asialo GM1+ cells (filled black squares, n=10) are shown according to the schema at the top of the figure. Percent survival is depicted on the y axis and time (days) on the x axis.

(FIG. 17A) In vivo bioluminescence analysis of effects of ganciclovir (GCV) treatment of 32Dp210-luc-HSV-TK+ leukemia. Mice inoculated IV with 32Dp210-luc-HSV-TK+ leukemia on day 0 were treated for 14 days with GCV (50 mg/kg) beginning at day 14. Left panel: Day 14 after tumor inoculation, Right panel: Day 28 after tumor inoculation and day 14 of GCV treatment. Total photon counts per mouse are depicted on the Y axis; Lanes N1-5: normal non-tumor bearing mice injected with luciferin; lanes 1-7, mice showing response to GCV, with total photon counts comparable to those of non-tumor bearing controls at day 28; lanes 8-10, mice that did not respond to treatment with GCV (FIG. 17B) Mean photon counts quantified by IVIS before and after GCV treatment in tumor bearing mice. Mean photon counts+S.E.M. per animal are plotted on the y-axis after imaging at day 14 (white bars) and day 28 after tumor inoculation (gray bars). Uninjected controls (n=5) represent normal, non-tumor bearing mice injected with luciferin to establish background levels of in vivo bioluminescence used to define "complete remission". MRD (minimal residual disease) indicates leukemic mice responsive to GCV that demonstrated background levels of in vivo bioluminescence after 14 days of treatment (MRD; n=7). Leukemic mice with tumor progression despite GCV administration (Non-responders, n=3) are depicted in the last two lanes on the right. (FIG. 17C) Demonstration of pathologic remission induction with 2 weeks of Ganciclovir treatment. Comparison of the percentage of 32Dp210-GFP+HSVTK+ cells in peripheral blood, spleen and bone marrow of responding mice (MRD). The percentage of GFP+ cells detected by flow cytometric analysis of blood (filled circle), spleen (open triangle), and bone marrow (filled diamonds) from each mouse achieving IVIS defined remission with MRD, are indicated on the Y axis. The mean for each group is designated by a horizontal line for each group as well as the S.E.M. Mice with MRD defined by semi-quantitative in vivo bioluminescence analyses had <5% leukemic cells in all tissues examined consistent with the clinical/pathological definition of leukemic remission.

(FIG. 18A) In vivo bioluminescence analyses of 32Dp210-luc-HSV-TK leukemic mice undergoing GCV treatment with or without post-remission vaccination with 32Dp210-CD80-IL-15-IL-15Rα cells. Mice were inoculated with 1×10$^5$ 32Dp210 cells on day 0 as indicated by the schema at the top of the figure. On day 10 mice underwent in vivo bioluminescence imaging and average photon counts per animal were plotted (upper set of bar graphs). N1-N5 represents normal, non-tumor bearing mice injected with luciferin on the same day, to establish background levels. Lanes 1-15 indicate mice inoculated with leukemia and subsequently treated with GCV according to the schema at the top of the figure. Gray bars in lanes 1-5 indicate IVIS analyses of mice that would receive 14 days GCV treatment and no further intervention; Black bars in lanes 6-15 depict IVIS analyses of mice treated with 14 days of GCV treatment that would be followed by serial vaccination with irradiated 32Dp210-IL-15/IL-15Rα/CD80 cells beginning at day 17. Lower panel of bar graphs depicts semi-quantitative IVIS studies after 5 days of GCV administration (day 15) in the same animals analyzed in the upper panel of bar graphs at day 10 after tumor inoculum. (FIG. 18B) Survival of 32Dp210-luc-HSV-TK leukemia bearing mice after remission induction with GCV treatment alone, versus GCV-mediated remission induction followed by administration of irradiated 32Dp210-IL-15/IL-15Rα/CD80 vaccine. Black filled circles: leukemia inoculation with no treatment (n=5); open circles: 14 day GCV treatment beginning day 10 after leukemia injection (n=5); filled black squares: GCV-mediated remission induction followed by serial vaccination with irradiated 32Dp210-IL-15/IL-15Rα/CD80 cells (n=10).

DETAILED DESCRIPTION OF THE INVENTION

Figure 1:
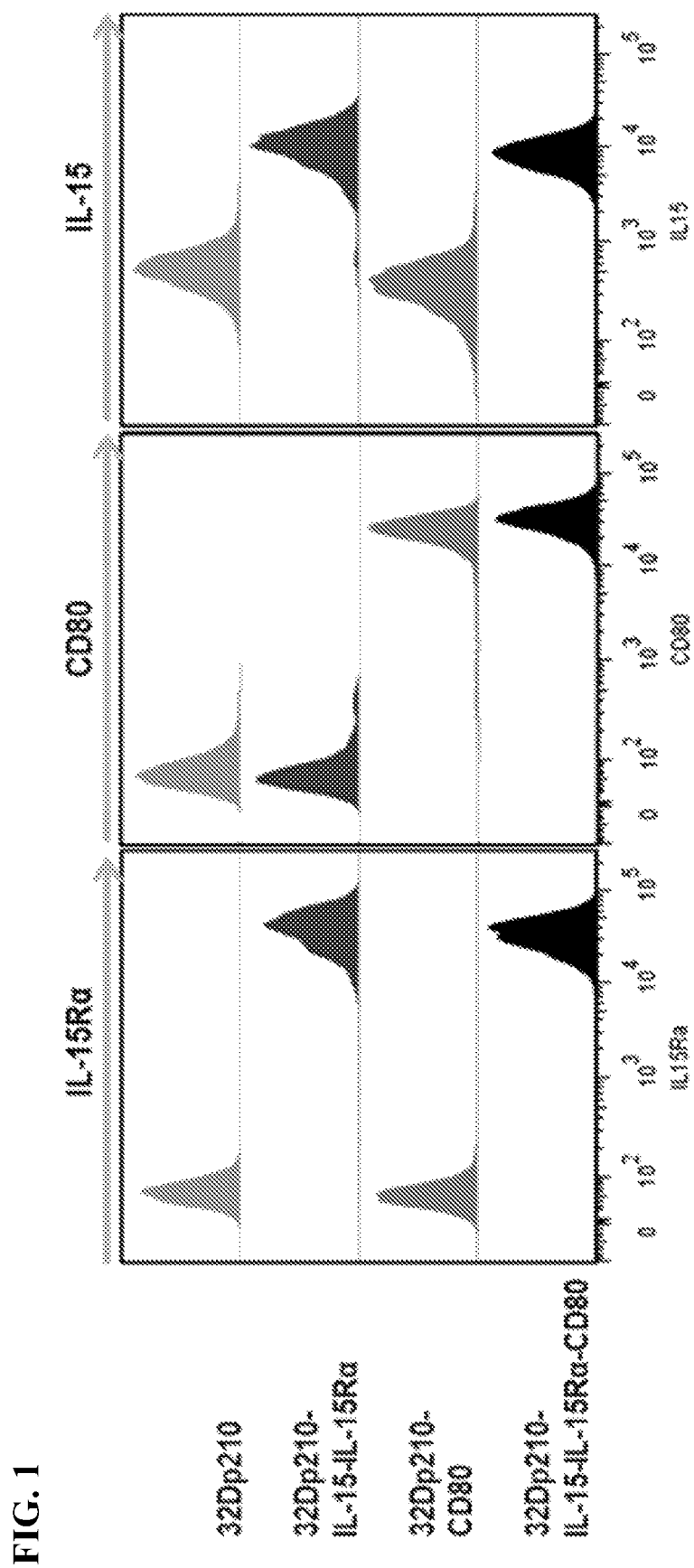
FIG. 1 shows cell surface expression of murine IL-15Ra, CD80, and IL-15 in 32Dp210 AML derived whole cell vaccines.

Provided herein, inter alia, are recombinant cell vaccines, cell media compositions, and methods of generating recombinant cell vaccine and cell media compositions, in either autologous or allogeneic settings. Methods and compositions of the present invention can be used in the treatment of leukemia (such as acute myeloid leukemia (AML)) by stimulation of an immune response to antigens on AML cells.

Cell media compositions of the present invention include whole cell vaccines. Cell media compositions of the present invention include multiple cell signaling molecules (e.g. IL-15, IL15-Rα, and CD80.) Signaling molecules of the cell media compositions disclosed herein can be excreted into the cell media, presented on the cell surface, or both. An advantage of the present invention is the potential to stimulate responses to multiple antigens. The whole cell vaccines of the present invention do not require definition of specific epitopes, or tailoring to individual HLA. Whole cell vaccines of the present invention are also readily cultured and transduced with lentiviral vectors after cryopreservation.

Known autologous vaccines have been previously described in which a) an engineered cell line expressing a cytokine (e.g., GM-CSF) is co-injected with irradiated tumor cells (i.e. GVAX; Borrello I M, Levitsky H I, Stock W, et al. Granulocyte-macrophage colony-stimulating factor (GM-CSF)-secreting cellular immunotherapy in combination with autologous stem cell transplantation (ASCT) as postremission therapy for acute myeloid leukemia (AML). *Blood* 2009; 114:1736-45), b) Tumor cells are fused with patient derived and ex vivo expanded dendritic cells (Rosenblatt J., Stone R. M., Uhl L., D. Avigan et al., Individualized vaccination of AML patients in remission is associated with induction of antileukemia immunity and prolonged remissions. *Science Transl. Med.* 2016; 8:368ra 171), or c) vaccines incorporating a variety of adjuvant molecules and peptides derived from common tumor associated antigens. These prior vaccines lack the ease of production and administration of the cell media compositions of the present invention. The cell media compositions of the present invention can be washed, treated, combined, supplemented, or otherwise altered prior to administration to a subject in need thereof. Furthermore, administration can be at varied doses, time intervals or in multiple administrations.

I. General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, Molecular Cloning: A Laboratory Manual, fourth edition (Sambrook et al., 2012) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2014); PCR: The Polymerase Chain Reaction, (Mullis et al., eds., 1994); Antibodies: A Laboratory Manual, Second edition, Cold Spring Harbor Laboratory Press, Cold Spring Harbor, NY (Greenfield, ed., 2014), Beaucage et al. eds., Current Protocols in Nucleic Acid Chemistry, John Wiley & Sons, Inc., New York, 2000, (including supplements through 2014), Gene Transfer and. Expression in Mammalian Cells (Makrides, ed., Elsevier Sciences B. V., Amsterdam, 2003), and Current Protocols in Immunology (Horgan K and S. Shaw (1994) (including supplements through 2014).

II. Definitions

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting.

The term "cancer" refers to or describes the physiological condition in mammals that is typically characterized by unregulated cell growth/proliferation. Examples of cancer include but are not limited to, blastoma, sarcoma, and leukemia (such as acute myeloid leukemia).

The term "relapse" or "relapsed" as used in the context of one or more of "relapsed cancer", "relapse of a cancer", "cancer relapse", or "tumor relapse" refer to the return or reappearance of cancer after a period of improvement. Typically the period of improvement is after administration of a therapy that resulted in the decrease of or disappearance of signs and symptoms of cancer. The period of improvement can be the decrease or disappearance of all signs and symptoms of cancer. The period of improvement can also be the decrease or disappearance of some, but not all, signs and symptoms of cancer. In some embodiments, the relapsed cancer is a cancer that has become unresponsive or partially unresponsive to a drug or a therapy. For example and without limitation, relapsed cancer includes cancer in patients whose first progression occurs in the absence of any treatment following successful treatment with a drug or a therapy; cancer in patients who progress on a treatment, or within 60 days of the treatment; and cancer in patients who progress while receiving treatment.

The phrase "minimal residual disease" (MRD) refers to small numbers of cancer cells (such as leukaemic cells) that remain in the subject during treatment, or after treatment when the patient is in remission (no symptoms or signs of disease). MRD is undetectable using conventional diagnostic techniques such as X ray, CT scan, or MRI, or techniques that detect tumors detectable by X ray, CT scan or MRI. MRD can be detected using cell-based detection techniques (such as, for example, immunofluorescence, FACS analysis, or in situ hybridization) or biochemical/molecular biological techniques (such as RT-PCR).

The term "modulation" of, e.g., a symptom, level or biological activity of a molecule, or the like, refers, for example, to the symptom or activity, or the like that is detectably increased or decreased. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self-assessment, by a clinician's assessment or by conducting an appropriate assay or measurement, including, e.g., assessment of the extent and/or quality of immunostimulation in a subject achieved by an administered immunogen. Modulation may be transient, prolonged or permanent or it may be variable at relevant times during or after a composition of the invention is administered to a subject or is used in an assay or other method described herein or a cited reference, e.g., within times described infra, or about 12 hours to 24 or 48 hours after the administration or use of a composition the invention to about 3, 4, 5, 6, 7, 8, 9, 10, 11, 12, 13, 14, 21, 28 days, or 1, 3, 6, 9 months or more after a subject(s) has received such an immunostimulatory composition/treatment. In embodiments, modulation is a stimulation (e.g., of an immune response).

As used herein, a "subject" or an "individual" or a "patient" includes animals that possess an adaptive immune system, or innate immune cells (e.g. NK cells), as described herein, such as human (e.g., human subjects) and non-human animals. The term "non-human animals" includes all vertebrates, e.g., mammals, e.g., rodents, e.g., mice, and non-mammals, such as non-human primates, e.g., sheep, dogs, cows, chickens, amphibians, reptiles, etc. In some embodiments, a subject is an elderly or geriatric subject (such as a patient at least about 60 years old, such as any of about 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more years old).

A "suitable dosage level" or a "therapeutically effective amount" refers to a dosage level that provides a therapeutically reasonable balance between pharmacological effectiveness and deleterious effects (e.g., sufficiently immunostimulatory activity imparted by an administered immunogen in the presence of a recombinant vaccine, or other vaccine derived from a cell media composition of the invention). For example, this dosage level can be related to the peak or average serum levels in a subject of, e.g., an anti-immunogen antibody produced following administration of an immunogenic composition at the particular dosage level. In other embodiments, a therapeutically effective amount is at least the minimum concentration required to effect a measurable improvement of a particular disorder. A therapeutically effective amount herein may vary according to factors such as the disease state, age, sex, and weight of the patient, and the ability of vaccine or therapy to elicit a desired response in the individual. A therapeutically effective amount may also be one in which any toxic or detrimental effects of the vaccine or therapy are outweighed by the therapeutically beneficial effects. In the case of cancer, the therapeutically effective amount of the oligonucleotide may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis: inhibit, to some extent, tumor growth; and/or relieve to some extent one or more of the symptoms associated with the cancer. To the extent the administered composition (such as any of the cell culture or whole cell vaccine cultures described herein) may prevent growth and/or kill existing cancer cells, it may be cytostatic and/or cytotoxic.

Administration "in combination with" one or more further therapeutic agents includes simultaneous (concurrent) and consecutive administration in any order.

As used herein, the term "lentivirus" refers to a group (or genus) of complex retroviruses that are also useful as a gene delivery vehicle or vector. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (Hy); bovine immune deficiency virus (BIV); and simian immunodeficiency virus (SIV). In one aspect, HIV based vector backbones (i.e., HIV cis-acting sequence elements) are preferred.

Retroviral vectors and more particularly lentiviral vectors may be used in practicing the present invention. Accordingly, the term "retrovirus" or "retroviral vector", as used herein is meant to include "lentivirus" and "lentiviral vectors" respectively.

The term "vector" is used herein to refer to a nucleic acid molecule or sequence capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In one aspect, a vector is a gene delivery vector. In one aspect, a vector is used as a gene delivery vehicle to transfer a gene into a cell.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus.

In particular aspects, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention. In embodiments, lentiviral transfection is used to transfect cells for whole vaccines. In embodiments, a lentiviral vector encodes a cytokine (e.g. IL-15, IL-15Rα, or CD80).

The phrase "recombinantly engineered" refers to cells that have been modified to express or overexpress one or more nucleic acids encoding one or more proteins. Non-limiting examples of common recombinant engineering techniques include transfection, transduction, and electroporation.

Unless specifically stated or obvious from context, as used herein, the term "or" is understood to be inclusive.

Unless specifically stated or obvious from context, as used herein, the terms "a", "an", and "the" are understood to be singular or plural.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"IL-15 or interleukin 15," as used herein is a cytokine that stimulates the proliferation of T-lymphocytes. Murine IL-15 is identified by, or largely homologous to UniProt P48346. Human IL-15 is identified by, or largely homologous to, UniProt P40933.

```
Murine IL-15 Amino Acid Sequence
                              (SEQ ID NO: 1)
MKILKPYMRN TSISCYLCFL LNSHFLTEAG IHVFILGCVS

VGLPKTEANW IDVRYDLEKI ESLIQSIHID TTLYTDSDFH

PSCKVTAMNC FLLELQVILH EYSNMTLNET VRNVLYLANS

TLSSNKNVAE SGCKECEELE EKTFTEFLQS FIRIVQMFINTS

Human IL-15 Amino Acid Sequence
                              (SEQ ID NO: 2)
MRISKPHLRSISIQCYLCLLLNSHFLTEAG

IHVFILGCFSAGLPKTEANW

VNVISDLKKIEDLIQSMHIDATLYTESDVH

PSCKVTAMKCFLLELQVISL

ESGDASIHDTVENLIILANNSLSSNGNVTESGCKECEELE

EKNIKEFLQSFVHIVQMFINTS
```

"IL-15Ra," or "IL-15Rα," or "interleukin 15 receptor subunit alpha," as used herein, is a high affinity receptor for IL-15. IL-15Rα can signal both in cis and trans where IL15Rα from one subset of cells presents IL15 to neighboring IL2RG-expressing cells. Expression of different isoforms may alter or interfere with signal transduction. Isoform 5, isoform 6, isoform 7 and isoform 8 do not bind IL15. Signal transduction involves SYK. Human IL-15Rα is identified by, or largely homologous to, UniProt Q13261. Murine IL-15Ra is identified by, or largely homologous to, UniProt Q60819.

```
Human IL-15Rα Amino Acid Sequence (SEQ ID NO: 3):
MAPRRARGCR TLGLPALLLL LLLRPPATRG ITCPPPMSVE

HADIWVKSYS LYSRERYICN SGFKRKAGTS SLTECVLNKA

TNVAHWTTPS LKCIRDPALV HQRPAPPSTV TTAGVTPQPE

SLSPSGKEPA ASSPSSNNTA ATTAAIVPGS QLMPSKSPST

GTTEISSHES SHGTPSQTTA KNWELTASAS HQPPGVYPQG

HSDTTVAIST STVLLCGLSA VSLLACYLKS RQTPPLASVE

MEAMEALPVT WGTSSRDEDL ENCSHHL

Murine IL-15Rα Amino Acid Sequence (SEQ ID NO: 4):
MASPQLRGYG VQAIPVLLLL LLLLLLPLRV TPGTTCPPPV

SIEHADIRVK NYSVNSRERY VCNSGFKRKA GTSTLIECVI

NKNTNVAHWT TPSLKCIRDP SLAHYSPVPT VVTPKVTSQP

ESPSPSAKEP EAFSPKSDTA MTTETAIMPG SRLTPSQTTS

AGTTGTGSHK SSRAPSLAAT MTLEPTASTS LRITEISPHS

SKMTKVAIST SVLLVGAGVV MAFLAWYIKS RQPSQPCRVE

VETMETVPMT VRASSKEDED TGA
```

"CD80," as used herein, is involved in the costimulatory signal essential for T-lymphocyte activation. T-cell proliferation and cytokine production is induced by the binding of CD28, binding to CTLA-4. Human CD80 is identified by, or largely homologous to UniProt P33681. Murine CD80 is identified by, or largely homology to, UniProt Q00609.

```
Human CD80 Amino Acid Sequence (SEQ ID NO: 5):
MGHTRRQGTSPSKCPYLNFFQLLVLAGLSHFCSGVIHVTKEVKEVATLSC

GHNVSVEELAQTRIYWQKEK KMVLTMMSGD MNIWPEYKNR

TIFDITNNLSIVILALRPSDEGTYECVVLKYEKDAFKREHLAEVTLSVKA

DFPTPSISDFEIPTSNIRRIICSTSGGFPEPHLSWLENGEELNAINTTVS

QDPETELYAVSSKLDFNMTT NHSFMCLIKYGHLRVNQTFN

WNTTKQEHFPDNLLPSWAITLISVNGIFVICCLTYCFAPR

CRERRRNERL RRESVRPV

Murine CD80 Amino Acid Sequence (SEQ ID NO: 6):
MACNCQLMQD TPLLKFPCPR LILLFVLLIR LSQVSSDVDE

QLSKSVKDKV LLPCRYNSPH EDESEDRIYW QKHDKVVLSV

IAGKLKVWPE YKNRTLYDNT TYSLIILGLV LSDRGTYSCV

VQKKERGTYE VKHLALVKLS IKADFSTPNI TESGNPSADT

KRITCFASGG FPKPRFSWLE NGRELPGINT TISQDPESEL

YTISSQLDFN TTRNHTIKCL IKYGDAHVSE DFTWEKPPED

PPDSKNTLVL FGAGFGAVIT VVVIVVIIKC FCKHRSCFRR

NEASRETNNS LTFGPEEALA EQTVFL
```

III. Cell Media Compositions and Whole Cell Vaccines

Cell media compositions of the present invention include cells grown in vitro and their culture media. In embodiments, cell media compositions are used as whole cell vaccines. In embodiments, cell media compositions of the present invention may administered in combination with traditional leukemia therapies (e.g. chemotherapy, targeted therapy, antibody mediated therapy etc.), immunotherapies (e.g., checkpoint inhibitors, immune stimulants), or combinations thereof. In embodiments, a co-therapy may be administered prior to, following, or concurrently with administration of the cell media compositions of the present invention.

In embodiments, cell media compositions include transfected or transduced recombinant cells. Generation of recombinant cells via transfection or transduction can be accomplished using techniques that are well known in the art. In embodiments, cell transfection is a lentiviral transfection. In embodiments, a lentiviral vector is a multicistronic vector (such as a bi-cistronic vector or a tri-cistrionic vector). In embodiments, a lentiviral vector is a tricistronic vector. In embodiments, vectors are codon optimized for their intended host cells.

In some embodiments, the recombinant cells used in any of the cell media compositions or whole-cell vaccines disclosed herein are cancer cells derived from an individual diagnosed with or thought to have a cancer (for example, leukemia, such as AML). Cancer cells may be obtained from a culture, tissue, organ or organism. In certain embodiments, the cancer cells can be autologous cancer cells from the individual being treated. In other embodiments, the cancer cells can be allogenic cancer cells. Those of skill in the art are familiar with methods for obtaining cancer cells from a subject. For example, the cancer cells may be obtained by biopsy, aspiration, surgical resection, venipuncture, or leukapheresis. In certain aspects, the cancer cells are expanded in culture prior to transfection or transduction.

Figure 19:
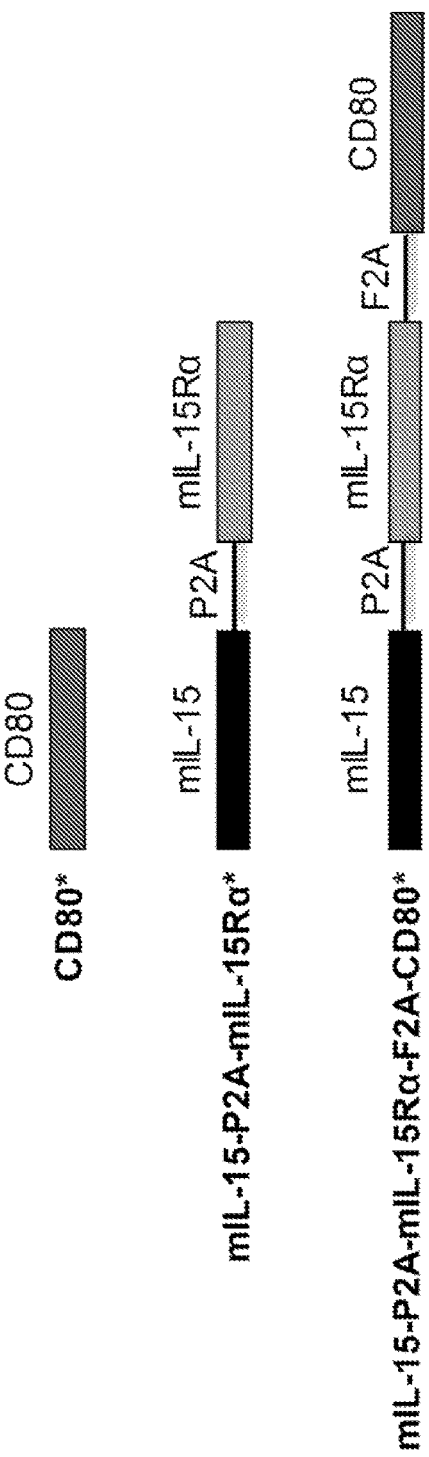
FIG. 19 depicts a lentiviral vector construct for use in one or more embodiments of the cell media compositions or whole cell vaccine compositions disclosed herein.

In certain embodiments, the cancer cell (such as a leukemia cell) is recombinantly engineered with nucleic acid molecules encoding at least 1, 2, or 3 immuno-stimulatory proteins (such as IL-15, IL-15Rα, and CD80). When a cancer cell is modified to express two or more immuno-stimulatory proteins, the immuno-stimulatory proteins may be encoded by the same nucleic acid molecule or they may be encoded by separate nucleic acid molecules. In one embodiment, the cancer cells are transfected or transduced with IL-15 and IL-15Rα. In some embodiments, the cancer cells are recombinantly engineered (for example, transfected or transduced) with nucleic acids encoding IL-15, IL-15Rα, and CD80. The cells can also be transduced using a lentiviral vector, such as the lentiviral vector construct depicted in FIG. 19.

In certain embodiments, disclosed herein compositions for eliciting an immune response to a cancer cell in a subject. For example, cancer cells recombinantly engineered with one or more nucleic acid molecules encoding one or more therapeutic proteins (such as IL-15, IL-15Rα, and CD80) may be administered to a subject as a cellular vaccine. A "cellular vaccine" or "whole cell vaccine" is a vaccine made from whole cancer cells. The vaccine may be preventative or therapeutic. A preventative vaccination is given prior to the subject developing a disease. A therapeutic vaccination is given to a subject who already has the disease.

In other embodiments, the present invention provides a vaccine comprising a cancer cell genetically modified to over express one or more proteins as compared to an unmodified cancer cell. In some embodiments the cancer cell is an autologous cancer cell derived from the subject to be treated with the vaccine. In other embodiments the cancer cell is an allogenic cancer cell. In some aspects, the cancer cell is inactivated. In certain embodiments, the one or more proteins are further defined as IL-15, IL-15Rα, and CD80. In some aspects, the vaccine further comprises a pharmaceutically acceptable carrier.

In further embodiments, it can be desirable to inactivate a whole cell vaccine or cell media composition disclosed herein prior to administering them to the subject. Those of skill in the art are familiar with methods for inactivating cells. Any method may be used as long as it allows the cells to express the therapeutic protein while preventing the cells from proliferating. A common approach to inactivating cancer cells is irradiation. For example, the cancer cells could be irradiated with between about 30 Gy and about 300 Gy using a cell irradiator for 30 minutes. In some embodiments, the whole cell vaccine or cell media composition is inactivated by a cytostatic agent or a cytotoxic agent. In another embodiment, the whole cell vaccine or cell media composition is co-transfected with a suicide gene, such as HSV-TK. A cancer cell transfected with HSV-TK could then be killed after it was administered to the subject by giving the subject ganciclovir. A combination of cell inactivating methods may also be used.

In addition to being recombinantly engineered with nucleic acid molecules encoding therapeutic proteins, the cancer cells may also be transfected with marker genes (such as a gene that produces a protein capable of generating a signal (such as a fluorescent signal). A marker gene encodes a protein that facilitates the detection of the cells in the whole cell vaccine or cell media compositions disclosed herein.

Cancer cells modified to express therapeutic proteins for administration to a subject are contemplated by the present invention. One of ordinary skill in the art would be familiar with techniques for administering cells to a subject. Furthermore, one of ordinary skill in the art would be familiar with techniques and pharmaceutical reagents necessary for preparation of these cells prior to administration to a subject.

In certain embodiments of the present invention, the cell media or whole cell vaccine compositions will be an aqueous composition that includes the recombinantly engineered cancer cells that have been modified to express one or more therapeutic proteins (such as IL-15, IL-15Rα and/or CD80). In certain embodiments, the recombinantly engineered cancer cell is prepared using cancer cells that have been obtained from the subject. However, cancer cells obtained from any source are contemplated by the present invention. The cancer cells may have been obtained as a result of previous cancer surgery performed on the subject as part of the overall cancer treatment protocol that is specific for the particular patient.

Aqueous compositions of the present invention comprise an effective amount of a solution of the recombinantly engineered cancer cells in a pharmaceutically acceptable carrier or aqueous medium. As used herein, "pharmaceutical preparation" or "pharmaceutical composition" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the recombinantly engineered cancer cells, its use in the therapeutic compositions is contemplated. Supplementary active ingredients can also be incorporated into the compositions. For human administration, preparations should meet sterility, pyrogenicity, general safety and purity standards as required by the FDA Center for Biologics.

The biological material should be extensively dialyzed to remove undesired small molecular weight molecules and/or lyophilized for more ready formulation into a desired vehicle, where appropriate. The recombinantly engineered cancer cells will then generally be formulated for administration by any known route, such as parenteral administration. Determination of the number of cells to be administered will be made by one of skill in the art, and will in part be dependent on the extent and severity of cancer, and whether the recombinantly engineered cancer cells are being administered for treatment of existing cancer or prevention of cancer. The preparation of the pharmaceutical composition containing the recombinantly engineered cancer cells of the invention disclosed herein will be known to those of skill in the art in light of the present disclosure.

Upon formulation, solutions will be administered in a manner compatible with the dosage formulation and in such amount as is therapeutically effective. The formulations are easily administered in a variety of dosage forms, such as the type of injectable solutions described above. For parenteral administration, the solution including the recombinantly engineered cancer cells should be suitably buffered. The recombinantly engineered cancer cells may be administered with other agents that are part of the therapeutic regiment of the subject, such as other immunotherapy or chemotherapy.

In embodiments, the cytokines and cell surface markers of the present invention can be modified. Modifications can include domain coding sequences; those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50 C, 6×SSC (sodium chloride/sodium citrate buffer) and 0.1% SDS (sodium dodecyl sulfate) indicate about 60-70% homology, hybridization and wash conditions of 50-65 C, 1×SSC and 0.1% SDS indicate about 82-97% homology, and hybridization and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2. ebi.ac.uk.

Sequences may be determined to be largely homologous at the amino acid or nucleic acid level if they have sequence homology of at least 70%, at least 80%, at least 90%, at least 95%, at least 96%, at least 97%, at least 98%, at least 99%, at least 99.5%, at least 99.9% or higher homology to a reference sequence.

The cell media compositions disclosed herein can include recombinant cells comprising IL-15, IL-15Rα, and CD80 wherein the cells are capable of expressing IL-15, IL-15Rα, and CD80 and (2) IL-15 in the media. In some embodiments, the recombinant cells express from about 150 to about 400 ng/mL, such as 200-300, 350-350, or 300-400 ng/mL of one or more of IL-15, IL-15Rα, and CD80 into the media.

IV. Treating with Whole Cell Vaccines or Cell Media Compositions

Administration of cell media compositions as described above, including whole cell vaccines can be used in the stimulation of an immune response. In embodiments, recombinant cells as described above are administered to a subject after induction of remission of AML with chemotherapy, or after autologous or allogeneic hematopoietic stem cell transplantation. In embodiments, cell media compositions or recombinant cells are administered to a subject in need of increasing a population of CD3+CD4+, or CD3+CD8+ T cells, memory CD8+ T cells, NK cells or NKT cells. In embodiments, cell media compositions or whole cell vaccines are administered to a subject having or suspected of having AML.

32Dp210 leukemia cell populations induce immune deviation early in the disease course with increased expression of PD-L1 on tumor cells and PD-1 on CD4+ and CD8+ T cell populations in the spleen. In embodiments, treatment with vaccines expressing both CD80 and IL-15/IL-15Rα show greater protective effects in a tumor challenge model than do vaccines expressing either CD80 or IL-15/IL15Rα, by inducing immunity largely mediated by CD3+CD8+ T cells. In embodiments, vaccination increases overall survival in the wake of tumor burden reduction even with re-challenge with leukemia. In embodiments, IL15 provides important advantages as an immunostimulatory cytokine in the context of aging patients.

In some embodiments, a whole cell vaccine or cell media composition disclosed herein is administered to a patient with leukemia (such as, AML) by any means known in the art. For example, whole cell vaccines or cell media compositions may be administered by intravenous injection, intramuscular injection, intratumoral injection, subcutaneous injection, or leukapheresis. It is also contemplated that the whole cell vaccine or cell media composition can be administered intranodally, intralymphaticly, or intraperitoneally. The whole cell vaccine or cell media composition can be administered to the subject at or near a tumor in the subject, or to a site from which a tumor has been surgically removed from the subject. However, it is not necessary that the whole cell vaccine or cell media composition be administered at the tumor site to achieve a therapeutic effect. Thus, in certain embodiments the whole cell vaccine or cell media composition may be administered at a site distant from the tumor site. Those of skill in the art will be able to determine the best method for administering the whole cell vaccine or cell media composition to an individual subject.

The present invention contemplates administration of cancer cells recombinantly engineered to express one or more therapeutic proteins (such as CD80 and IL-15/IL-15Rα) to a subject for the treatment and prevention of cancer. An effective amount of the recombinantly engineered cancer cells is determined based on the intended goal, for example tumor regression. For example, where existing cancer is being treated, the number of cells to be administered may be greater than where administration of recombinantly engineered cancer cells is for prevention of cancer. One of ordinary skill in the art would be able to determine the number of cells to be administered and the frequency of administration in view of this disclosure. The quantity to be administered, both according to number of treatments and dose, also depends on the subject to be treated, the state of the subject, and the protection desired. Precise amounts of the therapeutic composition also depend on the judgment of the practitioner and are peculiar to each individual. Frequency of administration could range from 1-2 days, to 2-6 hours, to 6-10 hours, to 1-2 weeks or longer depending on the judgment of the practitioner.

Longer intervals between administration and lower numbers of cells may be employed where the goal is prevention.

For instance, numbers of cells administered per dose may be 50% of the dose administered in treatment of active disease, and administration may be at weekly intervals. One of ordinary skill in the art, in light of this disclosure, would be able to determine an effective number of cells and frequency of administration. This determination would, in part, be dependent on the particular clinical circumstances that are present (e.g., type of cancer, severity of cancer).

In certain embodiments, it may be desirable to provide a continuous supply of the therapeutic compositions to the patient. Continuous perfusion of the region of interest (such as the tumor) may be preferred. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the doses are administered.

In embodiments, administration is by bolus injection. In some embodiments, administration is by intravenous infusion. In some embodiments, a whole cell vaccine in a dosage of about 1,000 cells, 10,000 cells, $1 \times 10^3$ cells, $1 \times 10^4$ cells, $1 \times 10^5$ cells, $1 \times 10^6$ cells, $1 \times 10^7$ cells or more, or in a range of about $1 \times 10^3$ to $1 \times 10^4$ cells, $1 \times 10^3$ to $1 \times 10^5$ cells, $1 \times 10^3$ to $1 \times 10^6$ cells, $1 \times 10^4$ to $1 \times 10^5$ cells, or $1 \times 10^5$ to $1 \times 10^6$ cells, $1 \times 10^6$ to $1 \times 10^7$ cells, $1 \times 10^7$ to $1 \times 10^8$ cells. In some embodiments, the cells are administered in a single administration. In some embodiments, cells are administered in multiple administrations, (e.g., once or more per week for one or more weeks). In some embodiments, doses are administered about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. In some embodiments, there are 1, 2, 3, 4, 5, 6, 7, 8, 9, 10, or more total doses. In some embodiments, 4 doses are administered, with a 3 week span between doses.

The whole cell vaccine compositions or cell media compositions described herein are capable of stimulating the proliferation of one or more immune cells, for example, one or more of CD3+CD8+ T cells, CD3+CD4+ T cells, memory CD8+ T cells, NK cells, and NKT cells relative to the proliferation of these cells in individuals who have not been administered one of the compositions disclosed herein. The immune cells can be stimulated to proliferate up to about 20 fold, such as any of about 2 fold, 3 fold, 4 fold, 5 fold, 6 fold, 7 fold, 8 fold, 9 fold, 10 fold, 11 fold, 12 fold, 13 fold, 14 fold, 15 fold 16 fold, 17 fold, 18 fold, 19 fold, or 20 fold or more compared to the proliferation of comparable cells in individuals who have not been administered one of the vaccine or cell media compositions described herein.

As discussed supra, any of the whole cell vaccine compositions or cell media compositions described herein can be administered in combination with one or more chemotherapeutics or anti-cancer therapies. In some embodiments, the one or more anti-cancer therapy is selected from the group consisting of chemotherapy, radiation therapy, and surgery. "Chemotherapy" and "anti-cancer agents" are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used herein. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (Podophyllum peltatum).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

In some aspects, the anti-cancer agent can be selected from remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, gefitinib (Iressa®), taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, or etoposide.

In other embodiments, the anti-cancer agent can be selected from bortezomib, cyclophosphamide, dexamethasone, doxorubicin, interferon-alpha, lenalidomide, melphalan, pegylated interferon-alpha, prednisone, thalidomide, or vincristine.

In some embodiments of any of the embodiments disclosed herein, the method further comprises administration of a compound that inhibits one or more immune checkpoint molecules. In some embodiments, the immune checkpoint molecule is one or more of CTLA4, PD-1, PD-L1, A2AR, B7-H3, B7-H4, or TIM3. In some embodiments, the compound that inhibits one or more immune checkpoint molecules is an antagonistic antibody. In some embodiments, the antagonistic antibody is ipilimumab, nivolumab, pembrolizumab, durvalumab, atezolizumab, tremelimumab, or avelumab.

In some aspects, the one or more anti-cancer therapy is radiation therapy. As used herein, the term "radiation therapy" refers to the administration of radiation to kill cancerous cells. Radiation interacts with molecules in the cell such as DNA to induce cell death. Radiation can also damage the cellular and nuclear membranes and other organelles. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray. Radiation also contemplated herein includes, for example, the directed delivery of radioisotopes to cancer cells. Other forms of DNA damaging factors are also contemplated herein such as microwaves and UV irradiation.

Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted. When the radiation comprises use of radioactive isotopes, the isotope may be conjugated to a targeting agent, such as a therapeutic antibody, which carries the radionucleotide to the target tissue (e.g., tumor tissue).

Surgery described herein includes resection in which all or part of a cancerous tissue is physically removed, exercised, and/or destroyed. Tumor resection refers to physical removal of at least part of a tumor. In addition to tumor resection, treatment by surgery includes laser surgery, cryosurgery, electrosurgery, and micropically controlled surgery (Mohs surgery). Removal of precancers or normal tissues is also contemplated herein.

V. Rodent Model of Post-Remission MRD

Also provided herein is a rodent model for assessing the effectiveness of vaccines and other therapies for preventing relapse and prolonging relapse-free survival individuals in remission for AML. To recapitulate a state of MRD in a rodent, a 32Dp210 leukemia cell line is engineered to express the herpes thymidine kinase (HSV-TK) suicide gene. Following administration of the engineered leukemia cells to the rodents followed by establishment of leukemia in the rodents over a period of 3-14 days (such as any of 3, 4, 5, 6, 7, 8, 9, 10, 11, 12, 13, or 14 days), a therapeutically effective amount of ganciclovir (GCV), is used to induce remission. Establishment of leukemia in the rodents can be measured by any means known in the art, such as by IVIS. Remission is arbitrarily defined as a level of bioluminescence comparable to background levels in age-matched, luciferin-injected normal rodents. As used herein, the term "rodent" refers to any member of the order Rodentia. Examples of rodents include, without limitation, mice, rats, squirrels, prairie dogs, porcupines, beavers, guinea pigs, and hamsters. In one embodiment, a rodent is a rat. In another embodiment, a rodent is a mouse.

The invention can be further understood by reference to the following examples, which are provided by way of illustration and are not meant to be limiting.

EXAMPLES

Example 1: Materials and Methods

Standardized transduced 32Dp210 lines have been established that express either murine CD80 and IL15/1L15Rα, IL15/IL15Rα, or individual and combination control constructs, using transduction with CD80/-IL-2 as a reference. Populations with similar levels of CD80, IL15Rα, and IL15 expression were purified by FACS and IL-15 secretion quantified by ELISA respectively, tested for stability in culture, and cryopreserved. For vaccination, 32Dp210-transduced lines will be thawed, cultured for 48 hours, irradiated, and $1-3\times10^6$ cells injected intradermally in 2 month old C3H/HeJ mice 1 week after injection of $1-10\times10^4$ 32Dp210-LG.

Example 2: Generation of Whole Cell Vaccines

Figure 20:
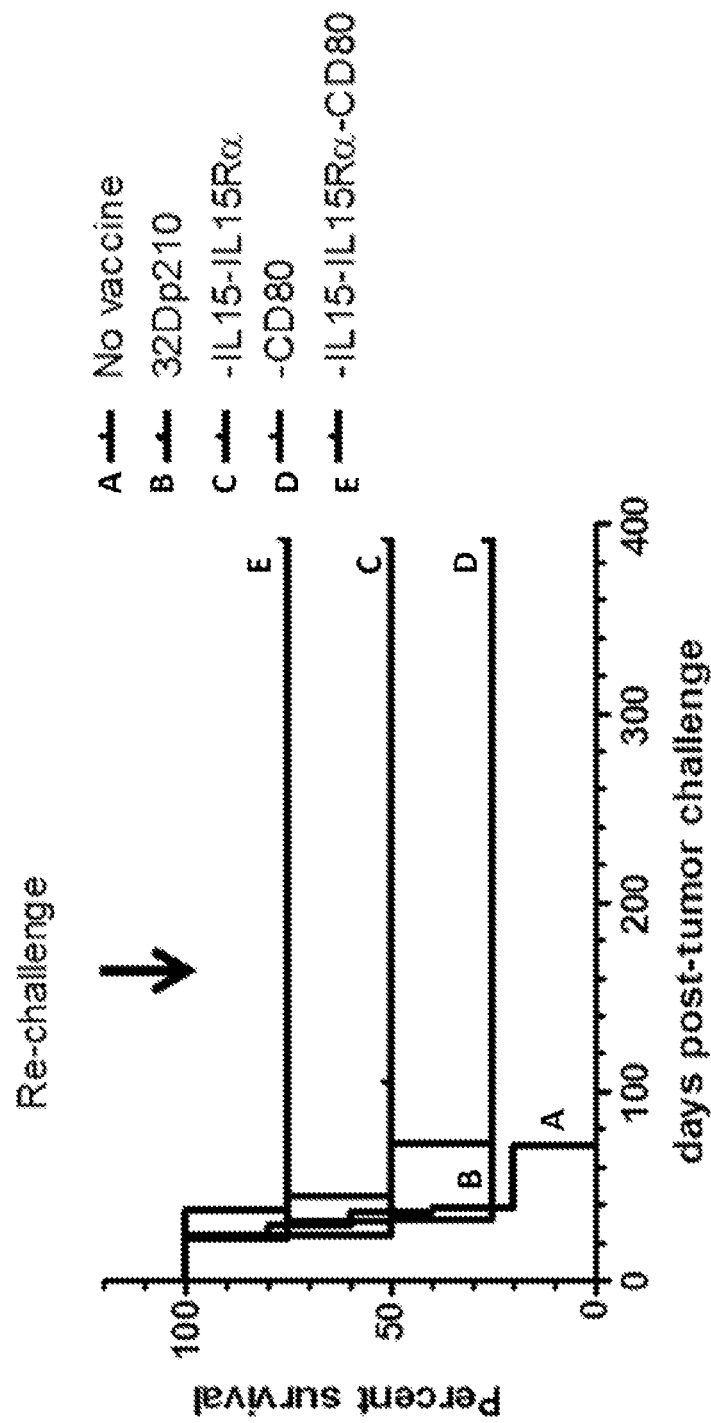
FIG. 20 depicts normal naïve C3H mice treated weekly four times with 2×10$^6$ irradiated 32Dp210-derived vaccines. Thereafter, they were initially challenged by IV injection of 10$^5$ 32Dp210-Luc leukemia cells, 2 weeks after last vaccination (day 0 on X axis). Leukemic progression was monitored by IVIS. Surviving mice were re-challenged by IV injection with 10$^5$ 32Dp210-Luc leukemia cells 24 weeks after the initial tumor challenge.

Irradiated whole cell AML vaccines, were generated by lentiviral-mediated transduction with CD80, IL-15/IL 15Rα, or both in 32Dp210 murine leukemia cells carrying the bcr-abl oncogene. Data demonstrates that, 1) compared to vaccines expressing CD80 or IL-15/IL-15Rα alone, 32Dp210 whole cell vaccines expressing both CD80 and IL-15/IL-15Rα stimulate greater CD4+ and CD8+ T cell proliferation in vitro. 2) In tumor challenge experiments where mice are first treated with irradiated AML vaccines (in the absence of tumor mediated immune deviation) and then challenged with leukemia cells, greater progression free (PFS) and overall survival (OS) is achieved with vaccines co-expressing CD80 and IL-15/IL-15Rα, than with vaccines expressing CD80 or IL-15 alone. FIG. 20 shows that 80% of mice survive after tumor challenge after vaccination with IL-15-IL-15Rα-CD80 expressing vaccine, 50% with IL-15Il-15Rα expressing vaccine, 25% with vaccine expressing CD80 alone or after vaccination with un-transduced irradiated 32Dp210 parent cells. 3) Improved survival outcomes have also been demonstrated with genetically engineered irradiated AML vaccines in therapeutic studies where mice are vaccinated after establishment of leukemia; 4) Stimulation of CD8+ T cell mediated cytolytic activity is an important mechanism underlying vaccine efficacy as in vivo depletion of CD8+ T cells abrogates the therapeutic effect. The efficacy of this whole cell vaccine approach will be tested in older AML patients ineligible for allo-transplant, after remission induction and limited consolidation chemotherapy. 5) To this end, models of minimal residual disease have been developed in which the efficacy of the CD80/IL 15/IL-15Rα-expressing vaccines are tested in leukemic mice. In these studies, none of the animals treated with chemotherapy alone survived, whereas 50% of leukemic mice treated with chemotherapy and CD80/IL-15/IL-15Rα expressing vaccine show long-term survival. These studies will directly inform the design of a Phase 1 clinical trial for AML patients >60 years of age, who are ineligible for HSCT.

Leukemic cell vaccines transduced with tricistronic lentiviral vector reliably express CD80, IL-15 and IL-15Rα and secrete IL-15 pre- and post-radiation. Irradiated vaccines stimulate both proliferation and cytolytic effects and expression of IFN γ in ex vivo studies of splenocytes from treated mice.

Example 3: Optimization of Antigen Presentation

Inefficient antigen presentation due to down-regulation of the critical co-stimulator CD80, and poor induction of leukemia-specific cytolytic activity has generally limited efficacy of autologous AML vaccines. In contrast, studies by King's college, London have shown that AML cells engineered to co-express IL-2 as an immunostimulant, and the co-stimulatory protein CD80, significantly increase survival in murine leukemia. Autologous AML vaccines expressing CD80/IL-2 are now in Phase 1 trial at King's College (Dr. Farzin Farzaneh and Dr. Ghulam Mufti; Chan L, Hardwick N, Darling D, et al. IL-2/B7.1 (CD80) fusagene transduction of AML blasts by a self-inactivating lentiviral vector stimulates T cell responses in vitro: a strategy to generate whole cell vaccines for AML. *Mol Ther* 2005; 11:120-31; Hardwick N, Chan L, Ingram W, Mufti G, Farzaneh F. Lytic activity against primary AML cells is stimulated in vitro by an autologous whole cell vaccine expressing IL-2 and CD80. *Cancer Immunol Immunother* 2010; 59:379-88; Ingram W, Chan L, Guven H, et al. Human CD80/IL2 lentivirus-transduced acute myeloid leukaemia (AML) cells promote natural killer (NK) cell activation and cytolytic activity: implications for a phase I clinical study. Br J Haematol 2009; 145:749-60); However, there are significant concerns that IL-2 stimulates not only cytolytic T and NK cells, but also immune inhibitory T regulatory cells (Treg).

To address this issue, AML cell vaccines were generated and engineered to express CD80, and IL-15/IL-15Rα. IL-15, a $\gamma_c$ chain cytokine that shares with IL-2 the ability to stimulate NK and CD8+ cytolytic T cells, has been shown to have unique properties suited to stimulating anti-tumor immunity. IL-15 is primarily transpresented by cells expressing IL 15Rα to responding cells expressing IL-15R subunits (IL2/15R~ and γ common (γc) sub-units). This is a unique signaling mechanism that requires that IL-15 is bound intracellularly by IL-15Rα and transported to the cell surface. Coexpression of IL-15 with membrane-bound IL-15Rα, as a secreted complex (IL-15/sIL15Rα) increases IL-15 stability and efficacy. IL-15 improves memory CD8+ T cell expansion, shows less Treg induction than IL-2, and can protect immune effectors from Treg suppression. Unlike IL-2, IL-15 does not cause activation induced cell death in stimulated T cells.

Example 4: Materials and Methods

Cell Lines

32Dp210 myeloid leukemia cells expressing the p210 transcript of bcr abl were utilized in the following Examples. To enable longitudinal studies of tumors in vivo, 32Dp210 leukemia cells were transfected with a luciferase vector (Capital Bioscience, Cat.VSL-0074, Gaithersburg, MD) and positive clones isolated with puromycin selection. Independent 32Dp210 cell lines were transduced with eGFP for flow cytometric analysis of leukemia cells, or with the herpes simplex thymidine kinase suicide gene (HSV-TK), to confer sensitivity to ganciclovir (GCV) and tumor-specific lethality after drug administration. For each experiment, fresh aliquots of tumor cells were thawed, briefly expanded in RPMI, 10% fetal bovine serum (FBS) (Gibco, Life Technology), and 1% glutamine, and then washed in PBS and injected intravenously (IV) via lateral tail vein. The 32Dp210-GFP+ and 32Dp210-HSV-TK+ cell lines showed comparable growth to the 32Dp210-Luc+ cells in vivo (data not shown).

Flow Cytometric Analyses

Antibodies to H-2DK (15-5-5), H-2Kk (36-7-5), H-2Kb (AF6-88.5) CD3 (2C11), CD4 (RM4-5), CD8 (53-6.7), CD25 (PC61), CD335 (29A-1.4), CD11b (M1/70), Ly-6G and Ly-6C (Gr-1), CD80 (16-10A1), IL-15 (16-7154-85), IL-15Rα (DNT15Ra), CD279 (J43), CD44 (IM7), CD62L (MEL-14), FoxP3 (FM23), IFNγ (14-4-4s) and Fc Block (2.4G2), PD-L1 (BV711 (Rat anti-mouse CD274, clone MIH5;) matched BV711-conjugated isotype control (mAb; rat IgG 2a), PD-1 (BV421 (Hamster anti-mouse CD279, clone J43)) were purchased from BD Biosciences (San Jose, CA). Cultured and tissue-derived cells were suspended in PBS, labeled with Fc block BD Biosciences (San Jose, CA), stained with the indicated antibodies as recommended. Intracellular staining for FoxP3 and IFNγ was performed using Cytofix/Cytoperm-Fixation/Permeabilization Kit (Becton Dickinson, Cat. No. 554714). Data were analyzed using FlowJo software (Treestar, Ashland, OR).

Lentivirus Construction and Transduction Protocol

Lentiviral vectors were constructed by homologous recombination in a lentiviral vector backbone pMLV-mIL-2-Furin-CD80, containing the MLV promoter, murine IL-2, and murine CD8032. The murine IL-2-Furin-CD80 cassette in this vector was replaced either with mouse CD80 alone, or with codon-optimized mouse IL-15 with the leader sequence GM-CSF to increase expression, and a RNA/ codon-optimized, membrane associated, complete IL-15Rα (mIL-15Rα)[17,33]. The IL-15 cassette was linked by a P2A sequence, to generate a self-cleaving peptide[34] producing mouse IL-15-P2A-mIL-15Rα. A tri-cistronic lentiviral vector was constructed by linking the murine IL-15-P2A-IL-15Rα to murine CD80 with an F2A sequence (coding for a second self-cleaving peptide)[35]3' to the IL-15-IL-15Rα cassette generating IL-15-P2A-IL-15Rα-F2A-CD80.

Lentivirus production and transduction was performed as described[36]. Lentiviral function was verified by antibody-mediated cell-surface staining of transduced 293T cells. Secretion of IL-15 was also quantified by ELISA (see infra). Lentiviral construct designations indicate genes present.

Generation of 32Dp210 Derived Vaccines

32Dp210 cells were transduced with vectors encoding the indicated transgenes in the presence of 8 μg/ml polybrene in 6-well plates. To achieve comparable levels of expression of mouse IL-15, IL-15Rα, and CD80 in 32Dp210 vaccines, the transduced lines were first purified based on high-level and comparable CD80 cell surface expression. Then, 32Dp210-IL-15-IL-15Rα+ cells with comparable expression of IL-15Rα to those in transduced and purified 32Dp210-IL-15-IL-15Rα-CD80 populations, were isolated and expanded.

Mice

Eight to ten week old female C3H mice were purchased from Charles River (San Diego, CA) and housed under pathogen-free conditions at UCSF. Experiments were conducted under the supervision of UCSF Institutional Animal Care and Use Committee (IACUC) according to approved protocol (AN108913-02A).

Vaccine Protocols

Lentivirally transduced or untransduced 32Dp210-luc parental cells were irradiated with 40Gy prior to subcutaneous (SC) administration as vaccines. At lower doses of irradiation, occasional viable tumors were observed after SC injection (unpublished studies). Tumor progression and responses to vaccinations were analyzed by sequential imaging in a Xenogen in vivo imaging system (IVIS), after intraperitoneal (IP) injection with 150 mg/kg Luciferin followed by anesthesia with 3% isofluorane. Images were analyzed using Living Image software (Xenogen, Alameda CA)

Minimal Residual Disease Model

At day 10 after IV injection of $1 \times 10^5$ 32Dp210-luc cells, all mice had detectable leukemia by IVIS, and began a 14 day treatment (50 mg/kg/day) with Ganciclovir (GCV) (APP Pharmaceuticals, LLC, Schaumberg, IL). A higher dose of 100 mg GCV/kg/day was administered to confirm that GCV had minimal or no effects on blood counts (Table 1). Complete remission was defined as a level of in vivo bioluminescence, measured in treated animals, that was comparable to the background levels measured in luciferin-injected, non-tumor bearing controls.

In Vivo Cell Depletion Studies

In vivo depletion of different cellular subsets was carried out by IP injection of antibodies on days 3, 10, and 17 after day 0 inoculation with $1 \times 10^4$ 32Dp210 cells. Depleting antibodies which included 100 μl diluted rabbit anti-mouse anti-Asialo-GM1, 500 μg rat-anti-mouse CD4, or 500 μg rat anti-mouse CD8 (BioXCell, West Lebanon, NH) produced greater than 90% depletion of the target cells, verified by staining for CD3, CD4, CD8 and NKp46 in blood, 1 day after injection.

Elispot Assays of IFN Gamma (IFN-γ) Production 96-well plates (MAIP S4510; Millipore, USA) were coated with anti-IFN-γ antibody, washed, and blocked per manufacturer's instructions (Mabtech, USA). Spleen cells ($3 \times 10^5$) from vaccinated mice were plated in duplicate with an equivalent number of irradiated (100Gy) 32Dp210 cells, and incubated at 37° C. and 5% CO2 for 20 hours. Plates were developed by incubation with biotinylated anti-IFN-γ antibody (Mabtech, USA) according to manufacturer and activity detected using a colorimetric AP kit (Bio-Rad, CA, USA) and counted using an ELISpot reader (Cellular Technology Ltd.).

T Cell Proliferation Assay

Splenocytes from naïve mice were labeled with CellTrace Violet or CFSE; $2 \times 10^6$ cells were co-cultured with an equal number of irradiated (100Gy) 32Dp210-Luc, 32Dp210-Luc-IL-15-IL-15Rα, 32Dp210-Luc-CD80 or 32Dp210-Luc-IL-15-IL-15Rα-CD80 cells for 12 days. Co-cultured splenocytes were then stained with anti-CD3, anti-CD4, and anti-CD8 antibodies (see supra), and proliferation quantified by flow cytometric analyses[37].

T Cell Cytolytic Assay

Splenocytes harvested after 4 weekly vaccinations with 32Dp210, 32Dp210-IL-15-IL-15Rα, 32Dp210-CD80 or 32Dp210-IL-15-IL-15Rα-CD80 cells were re-stimulated in vitro with irradiated 32Dp210 parental cells for 5 days. These cells were purified over FiColl gradients and used as effectors. Target 32Dp210 cells were labeled with CellTrace DDAO-SE. Splenic effector cells were co-cultured at the indicated ratios for 24 or 48 hours with ($1 \times 10^5$) 32Dp210 target cells. The fractions of apoptotic 32Dp210 cells were determined by staining for active Caspase-3, using the Active Caspase-3 apoptosis kit (BD Bioscience) and FACS.

Measurement of IL-15

Concentrations of mIL-15 in culture supernatants were determined by ELISA using recombinant mouse IL-15 as a standard and a polyclonal rabbit anti-mouse IL15 antibody (H114, Santa Cruz Biotechnology, Inc., Santa Cruz, CA) as described by the manufacturer.

Statistical Analyses

All experiments were repeated at least two times unless indicated otherwise. Statistical analyses were performed using Prim 6 (GraphPad Software, Inc, La Jolla, CA) Results are reported as the mean±SE of independent experiments. The significance of differences was determined using Student's paired t-test.

Figure 7:
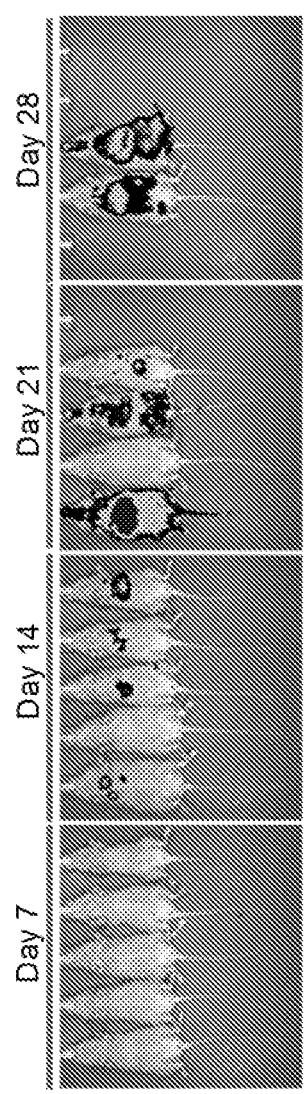
FIG. 7 depicts progression of 32Dp210 leukemia. IV injection of tumor cells produces systemic leukemia and 4-5 week survival in animals followed by in vivo bioluminescence studies. Upper panel: Serial in vivo bioluminescence images of C3H mice on days 7, 14, 21, and 28 after IV inoculation of $1\times10^4$ 32Dp210 leukemia cells on day 0, documenting rapidly progressive leukemia are shown. Lower panel: left: graph of the percentage of PD-1 expressing T cells in naïve versus tumor-bearing mice (white bar=naïve mice, gray bar=tumor-bearing mice); Middle panel: the percent PD-1 expressing CD3+CD8+ T cells in naïve versus tumor-bearing mice: (white bar=naïve mice, gray bar=tumor-bearing mice) Right panel: the level of PD-L1 expression on 32Dp210-GFP+ cells in culture and after transplantation in vivo: ((white bar=cultured 32Dp210, gray bar=32Dp210 cells harvested from tumor-bearing mice).
Figure 7:
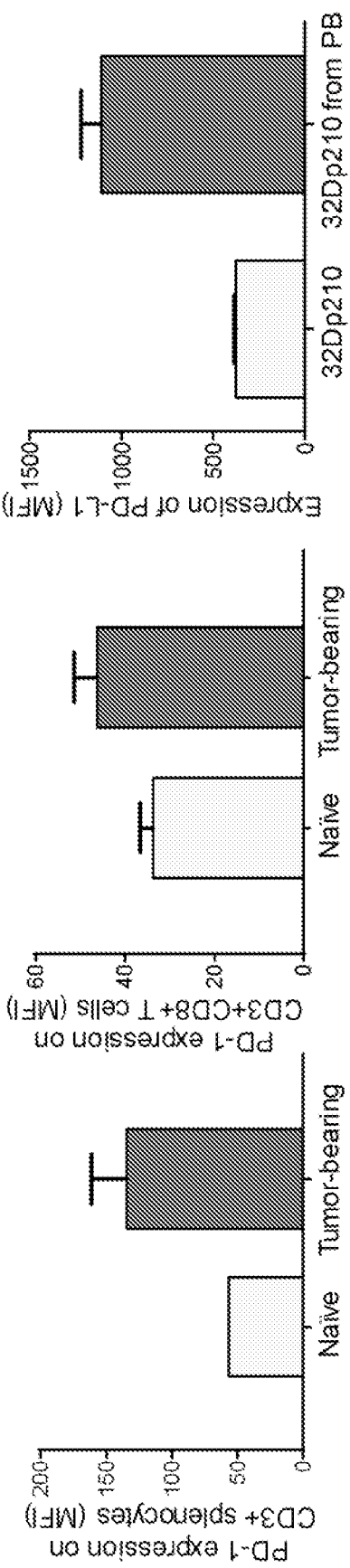
Figure 8A:
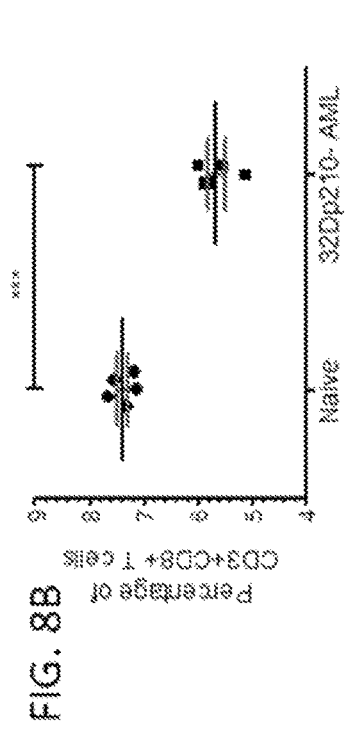
FIG. 8A-FIG. 8J depicts effects of 32Dp210 leukemia on immune effector populations in the spleen. Splenic populations were compared 14 days after leukemia inoculation in normal C3H mice (left panels) and in 32Dp210 leukemia-bearing mice (right panels). The percentage of each cell type in each subject are indicated.
Figure 8B:
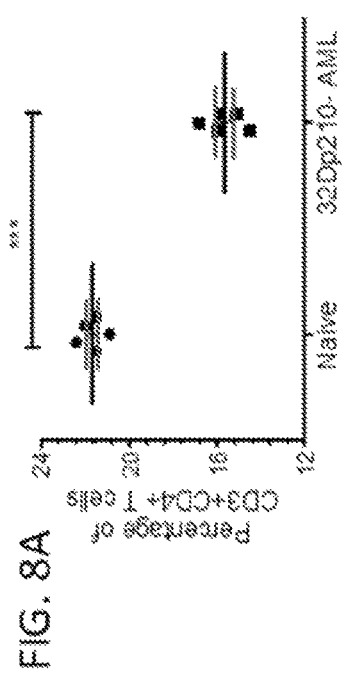
Figure 8C:
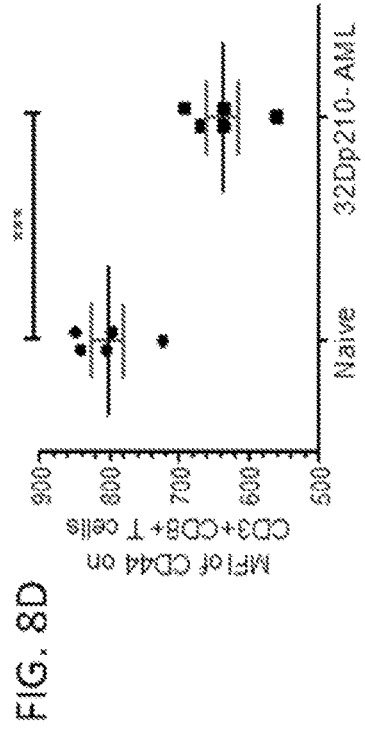
Figure 8D:
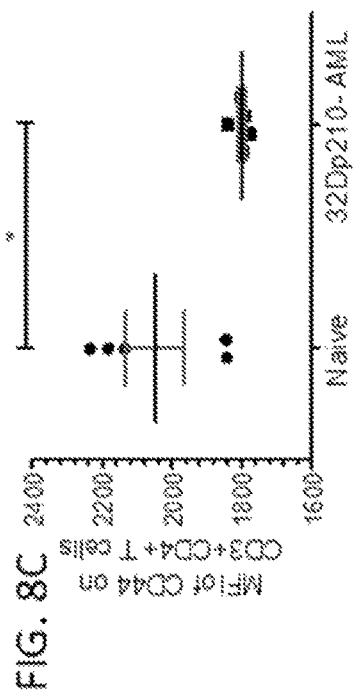
Figure 8E:
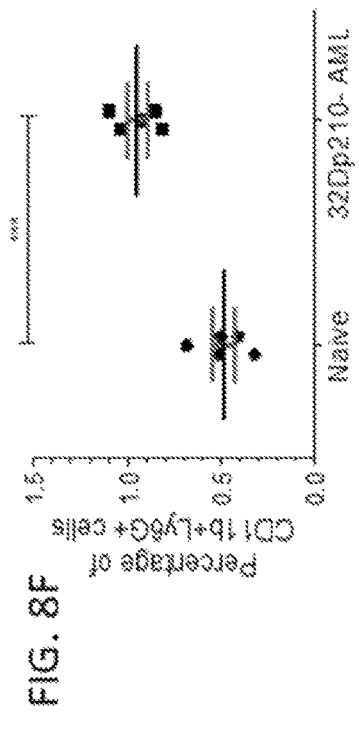
Figure 8F:
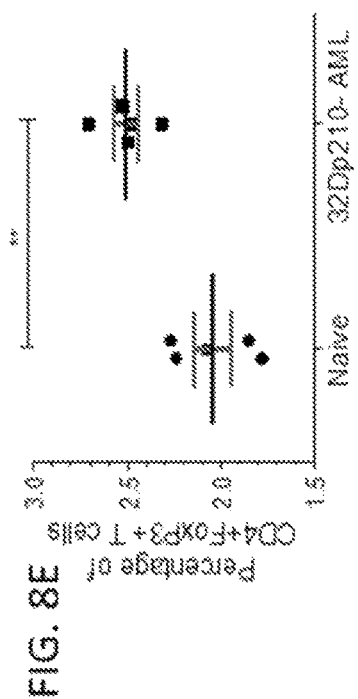
Figure 8H:
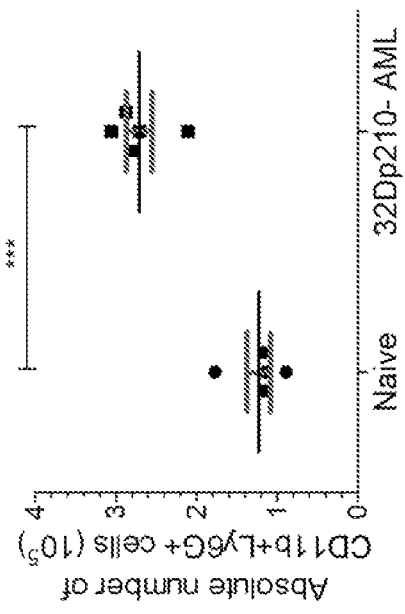
Figure 8G:
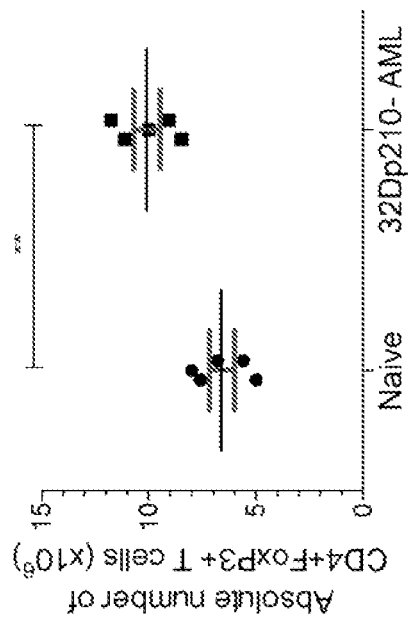
Figure 8J:
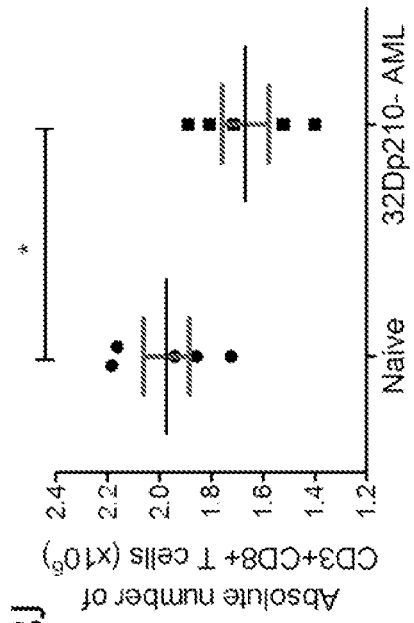
Figure 8I:
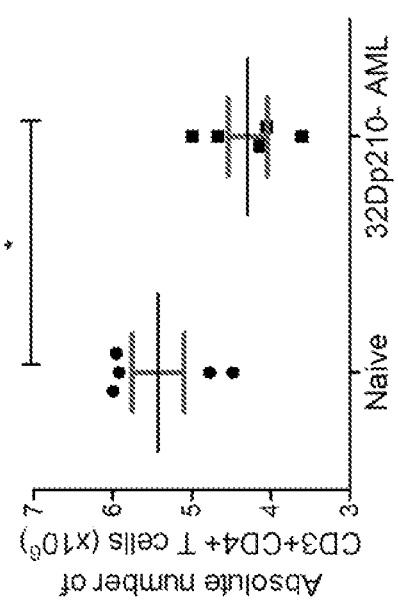
Figure 9:
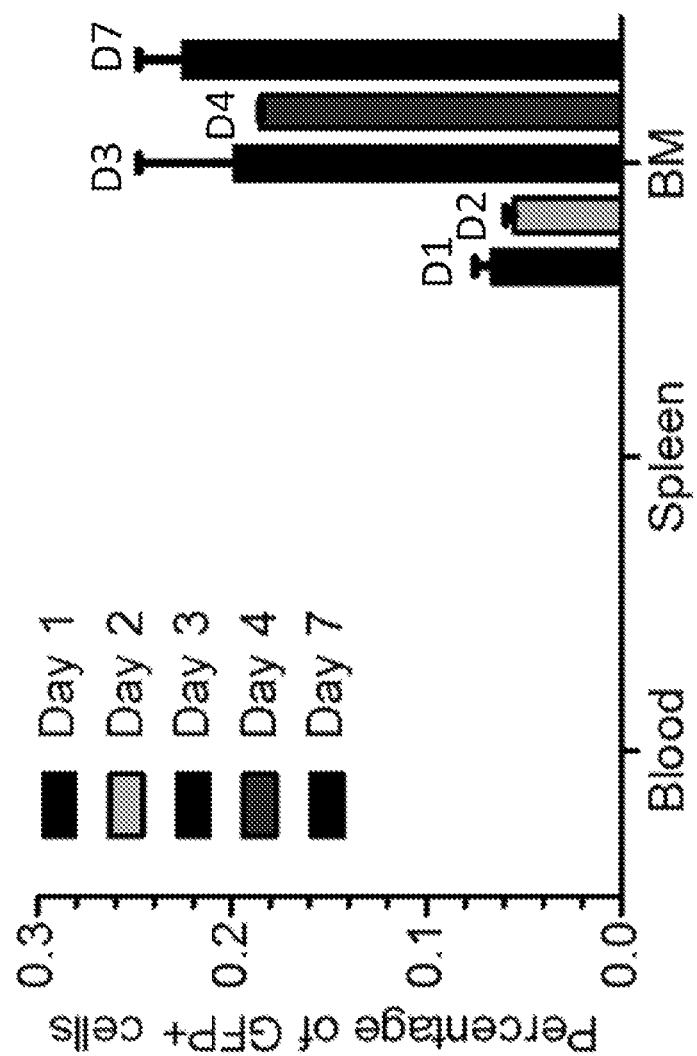
FIG. 9 depicts 32Dp210-GFP+ leukemia cells home to the bone marrow compartment early in disease. Bone marrow, spleen and peripheral blood were monitored by flow cytometric analyses on days 1, 2, 3, 4, and 7 after IV injection in C3H mice. (depicted as sequential bar graphs from left to right). The mean percentage of GFP+ cells in each tissue is indicated on the Y axis. Error bars=S.E.M.

Example 5: The 32Dp210 Leukemia Model Recapitulates Many Features of Clinical AML The assessment of immunotherapeutic approaches for AML have sometimes been precluded by the rapidity of progression after IV administration limiting the development of immune responses[38-40]. Dose-finding studies with 32Dp10 leukemia demonstrated that the minimal IV cell dose that reliably resulted in leukemic engraftment, and adequate survival to allow induction of immunity, was $1 \times 10^4$ cells (FIG. 7). Since leukemia-associated stimulation of inhibitory immune responses poses significant hurdles for the successful induction of clinically effective anti-leukemic immunity[9], we assessed whether early progression of 32Dp210 leukemia had comparable immunosuppressive effects. Analysis of splenocytes from mice 14 days after 32Dp210 inoculation showed an increase in the expression of the negative regulatory receptor PD-1 on T cells, and up-regulation of the PD-1 ligand, PD-L1 on engrafted 32Dp210 cells (FIG. 7, lower panels). The percentage of CD3+CD4+ T cells, CD3+CD8+ T cells, and the frequency of CD3+CD8+CD44$^{hi}$ T cells were all decreased, while the numbers of inhibitory CD4+FoxP3+ regulatory T cells (Treg) and CD11b+Ly6G+ myeloid derived suppressor cells (MDSC) were increased in leukemic mice (FIG. 8A-FIG. 8J). Thus, 32Dp210 leukemia produces broad immunosuppressive effects, similar to those observed in human AML.[9] 32Dp210 leukemia also recapitulated the tissue sites of homing seen clinically, as leukemia cells were first detected in the bone marrow during the first week of engraftment (0.2% GFP+ cells at day 3), but not in peripheral blood or spleen (FIG. 9).

Example 6: Transduction With Multicistronic Lentiviral Vectors Results in Appropriate Processing and Expression of IL-15, IL-15Rα, and CD80

Figure 2:
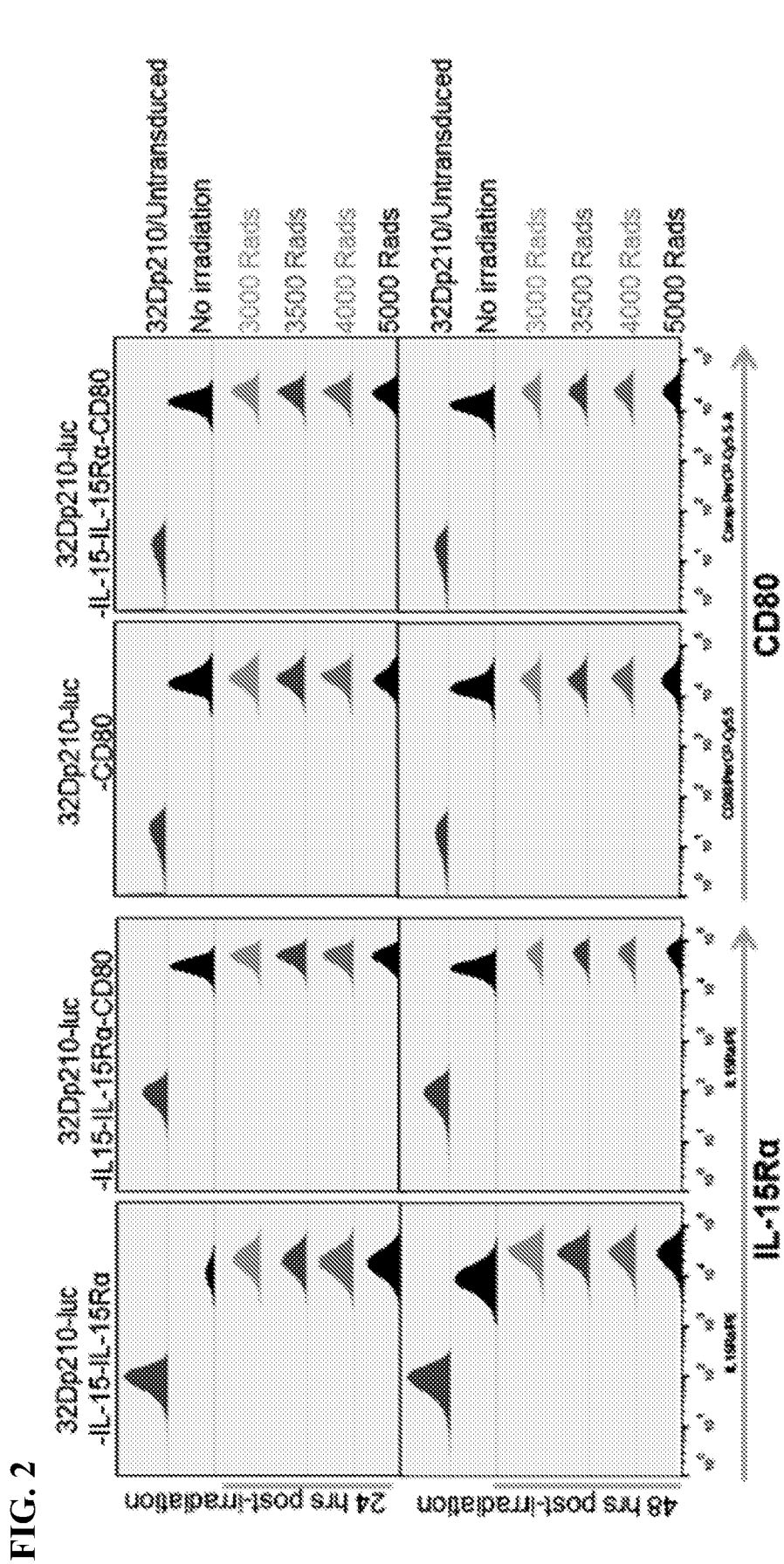
FIG. 2 shows transgene expression post-irradiation in 32Dp210-Luc whole cell vaccines.
Figure 10A:
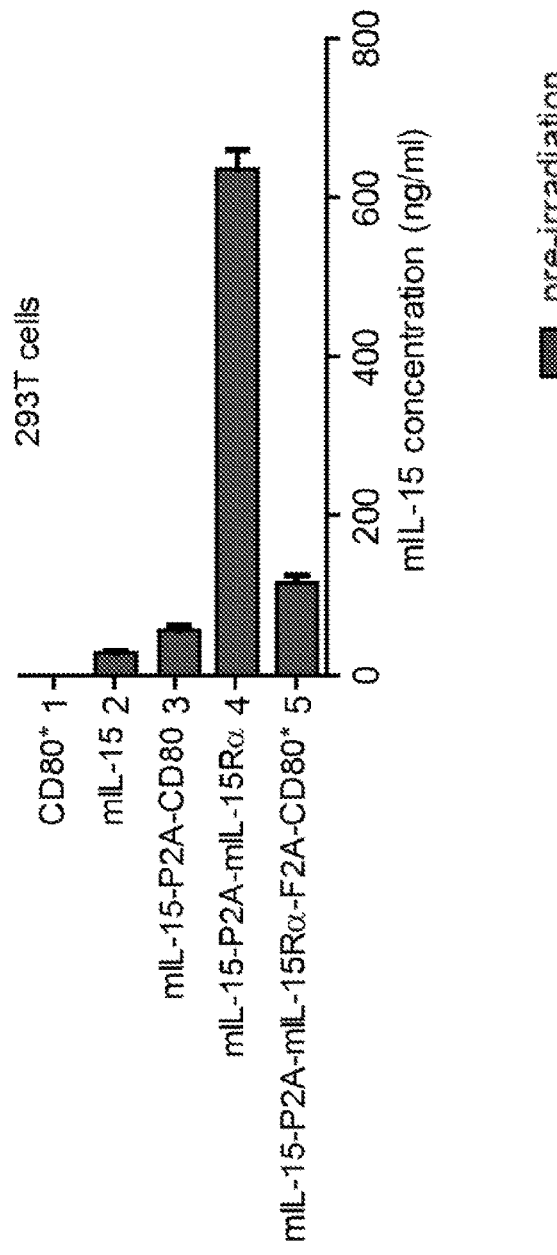
FIG. 10A-FIG. 10B depict appropriate processing and expression of IL-15, IL-15Rα, and CD80 are observed after lentiviral transduction of 293T and 32Dp210 cell lines.
Figure 10B:
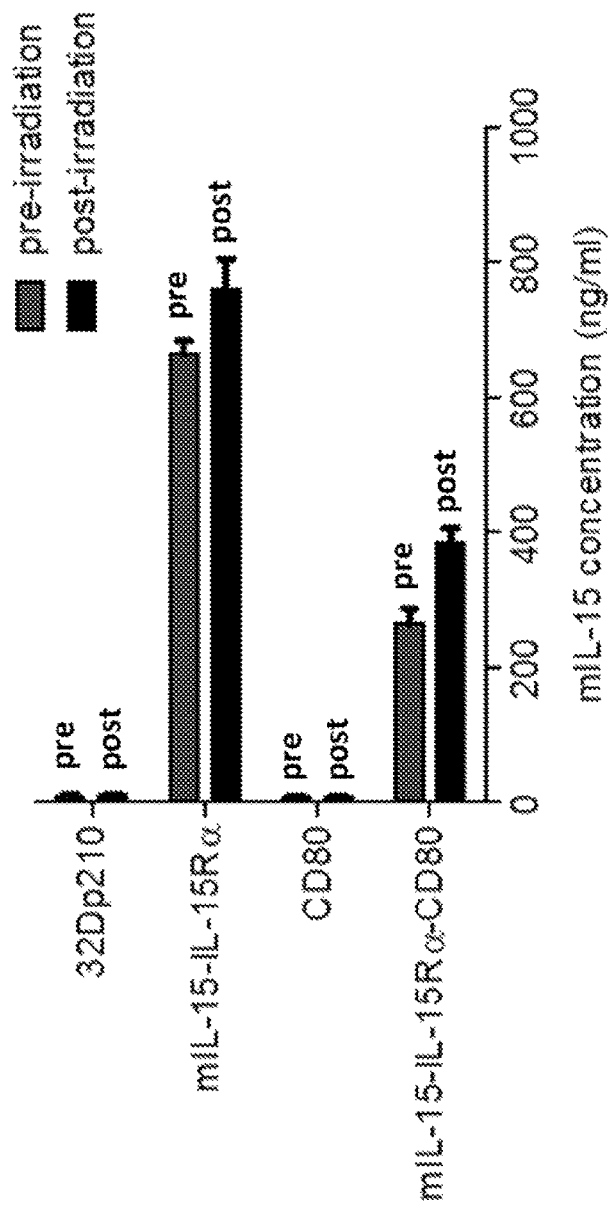
Figure 11:
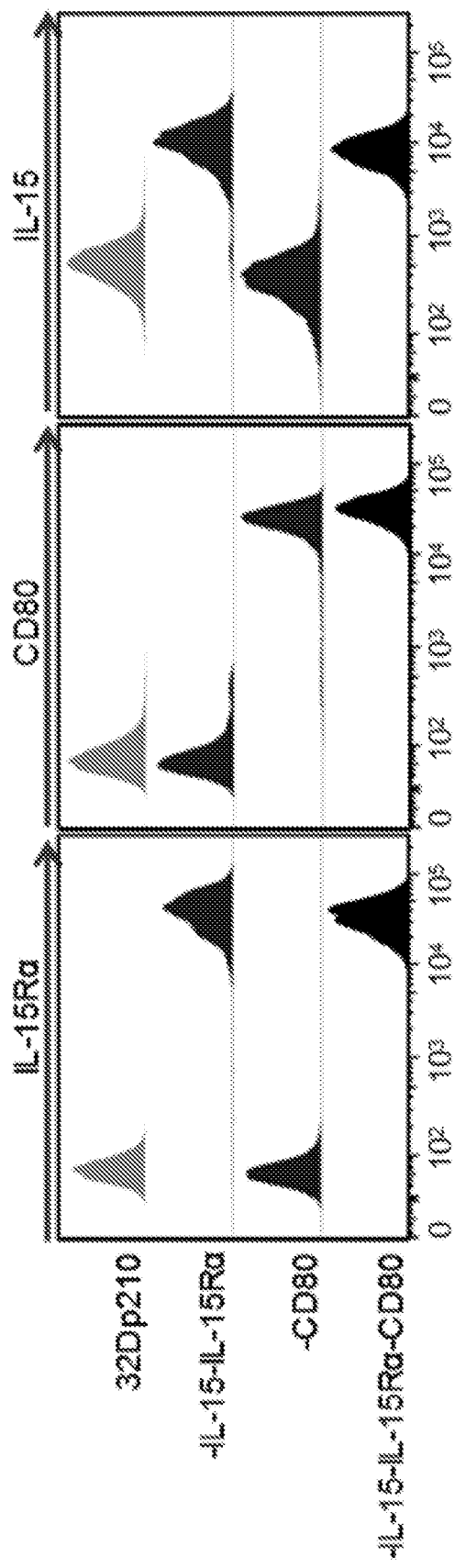
FIG. 11 depicts cell-surface expression of IL-15Rα, CD80, and IL-15 after FACS and purification of 32Dp210 populations. Lentivirally transduced, purified 32Dp210-derived cells were stained with anti-IL-15, anti-IL-15Rα and anti-CD80 antibodies, and expanded cell populations subjected to flow cytometric analysis. 32Dp210 on the left indicates the parental untransduced cell line as a control. The genes encoded by each lentiviral vector used to transduce the 32Dp210 cells are indicated to the left of the flow analysis, and the antibody used to stain cells is indicated above each flow plot.
Figure 12:
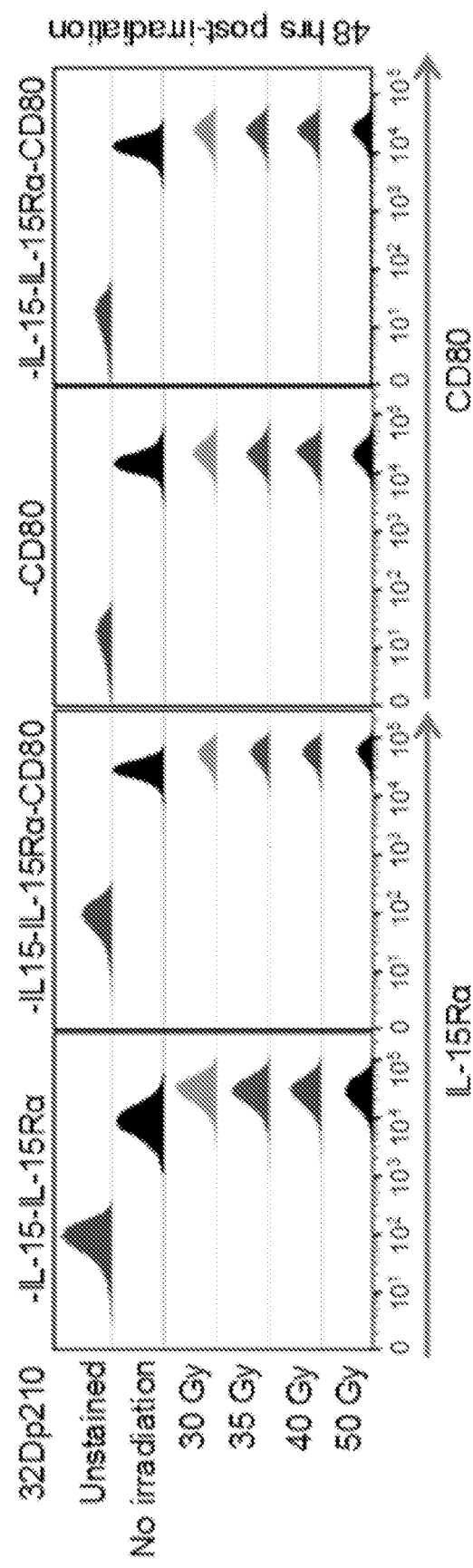
FIG. 12 depicts cell-surface expression of IL-15Rα and CD80 on 32Dp210 vaccines 48 hours after irradiation ex vivo. Lentivirally transduced, purified 32Dp210 cells were stained with anti-IL-15Rα and anti-CD80 antibodies and the effects of different doses of radiation on IL-15Rα and CD80 expression were analyzed. The lentiviral vector used to transduce 32Dp210 cells is indicated above each plot. Data showing cell surface IL-15Rα expression is shown in the left two graphs and cell surface staining with anti-CD80 antibodies is presented in the right two graphs. Antibodies used to analyze cell surface expression are indicated below the plots.

Since co-expression of IL-15 and IL-15Rα increases the secretion, half-life, and bio-activity of IL-15, lentiviral vectors were constructed that include both codon-optimized murine IL-15, and a membrane-associated murine IL-15Rα construct[17,33]. While IL-15 was barely detected in supernatants of transduced 293T cells in the absence of IL-15Rα, co-expression of IL-15 and IL-15Rα after transduction resulted in high levels of IL-15 secretion (FIG. 10A). Transduction with the IL-15-IL-15Rα-CD80 vector produced somewhat lower levels of IL-15 secretion both in 293T, (FIG. 10A) and in 32Dp210 cells (FIG. 10B). Thus the membrane associated IL-15-IL-15Rα construct is also cleaved to generate secreted IL-15. Lentivirally transduced 32Dp210 cell lines were serially purified by FACS to isolate populations with comparable IL-15Rα, CD80, and IL-15 cell surface expression (FIG. 1 and FIG. 11). The expression of transgenes in 32Dp210 cells was assessed at different dose levels of radiation to recapitulate conditions for in vivo administration. IL-15 secretion (FIG. 10B), and cell-surface IL-15Rα and CD80 expression (FIG. 2 and FIG. 12) were stable 48 hrs after irradiation with up to 50Gy.

Figure 3:
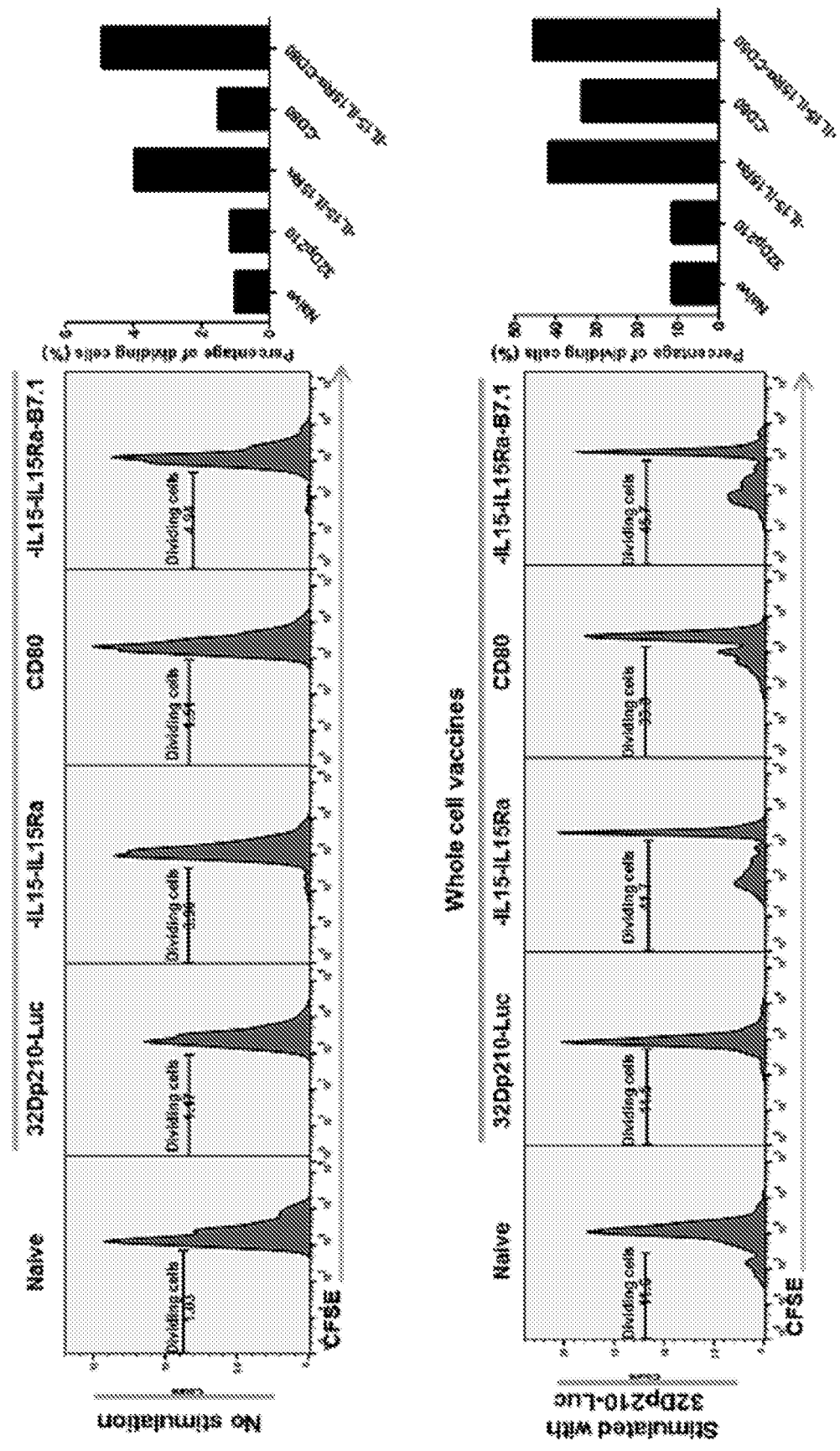
FIG. 3 shows in vitro proliferation of CD3+CD8+ splenocytes of C3H mice vaccinated with irradiated 32Dp210-Luc cell lines.
Figure 13A:
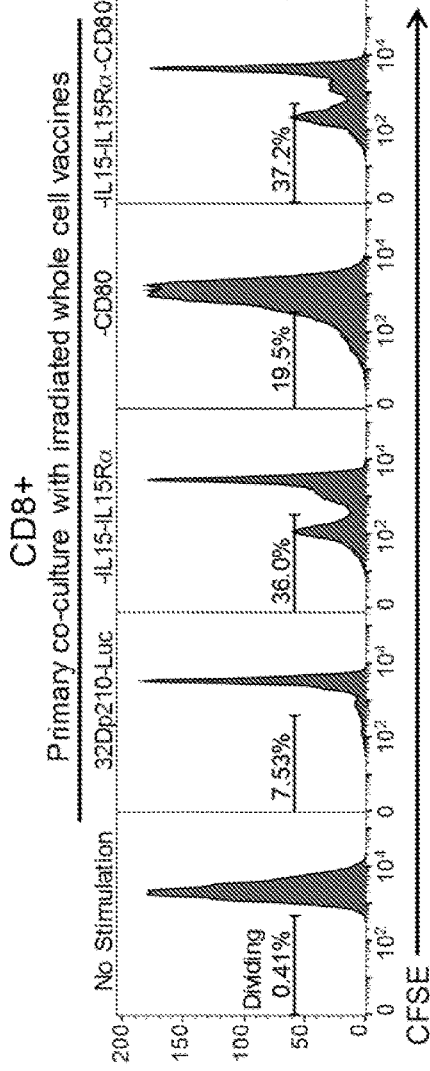
FIG. 13A-FIG. 13B depict co-culture of splenocytes from naïve mice vaccinated with transduced, irradiated 32Dp210-derived vaccines stimulates proliferation of CD3+CD4+ and CD3+CD8+ T cells. Splenocytes were labeled with CFSE, and cultured alone (No stimulation), or in the presence of irradiated 32Dp210 cells transduced with lentiviral vectors carrying CD80, IL-15-IL-15Rα or IL-15-IL-15Rα-CD80 (as depicted above each graph) for 12 days. The percent of dividing cells is indicated in each plot. After co-culture, cells were stained with anti-CD3, anti-CD8, and anti-CD4 antibodies, and quantified by flow cytometric analyses.
Figure 13B:
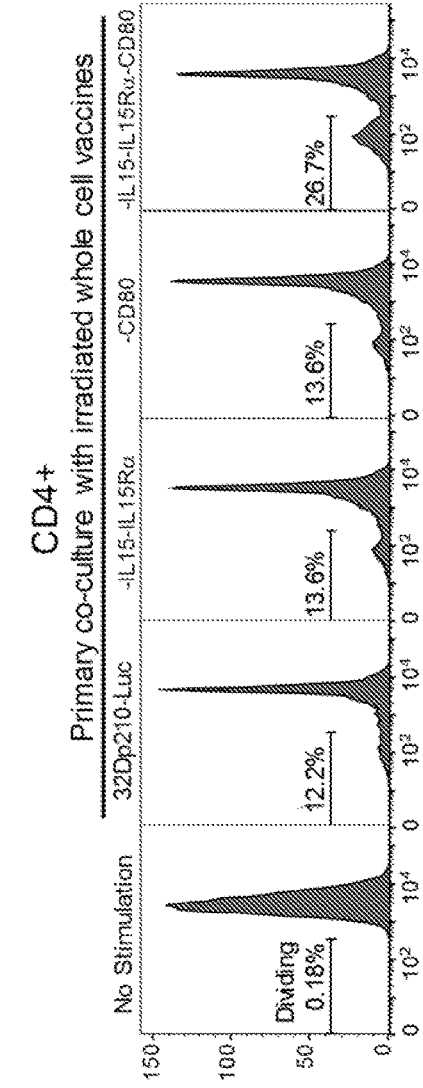

Example 7: 32Dp210-Derived Vaccines Stimulate Ex Vivo T Cell Proliferative Responses in Splenocytes from Naïve Mice Primary stimulation of splenocytes from naïve mice by co-culture with irradiated 32Dp210-IL-15-IL-15Rα or 32Dp210-IL-15-IL-15Rα-CD80 stimulated a five-fold increase in CD3+CD8+ T cell proliferation compared with co-culture with untransduced 32Dp210 cells (FIG. 3 and FIG. 13A). Lower levels of proliferation were observed with co-culture with 32Dp210-CD80. In the case of CD3+CD4+ splenocytes, proliferation stimulated by co-culture with either parent 32Dp210 cell vaccine, 32Dp210-CD80, or 32Dp210-IL-15-IL-15Rα-CD80 was comparable (FIG. 3 and FIG. 13B); however, primary stimulation of naïve CD3+CD4+ T cells with 32Dp210-IL-15-IL-15Rα-CD80 produced the greatest increase in proliferative responses consistent with additive effects of CD80 mediated co-stimulation and immune stimulation by IL-15.

Figure 14A:
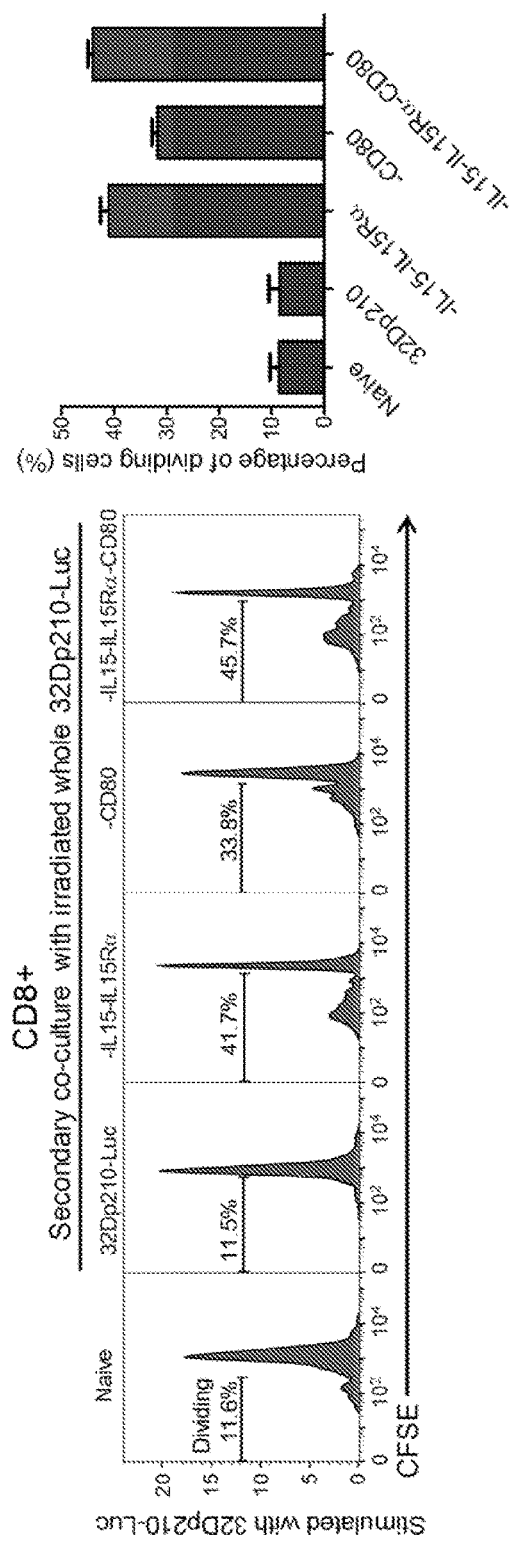
FIG. 14A-FIG. 14B depict T cell proliferation assays from vaccinated non-tumor bearing C3H mice: Splenocytes from C3H mice vaccinated weekly for a month with irradiated 32Dp210, 32Dp210-IL15-IL15Rα, 32Dp210-CD80 or 32Dp210-IL15-IL15Rα-CD80 cell vaccines were harvested, labeled with CFSE or CellTrace DDAO-SE, and co-cultured for 12 days with 32Dp210 parent cells treated with 100 Gy γ-irradiation. Thereafter, co-cultured splenocytes were immune-stained with anti-CD3, CD4, and CD8 antibodies, and proliferation quantified by flow cytometry. The percent of dividing cells is indicated in each plot.
Figure 14B:
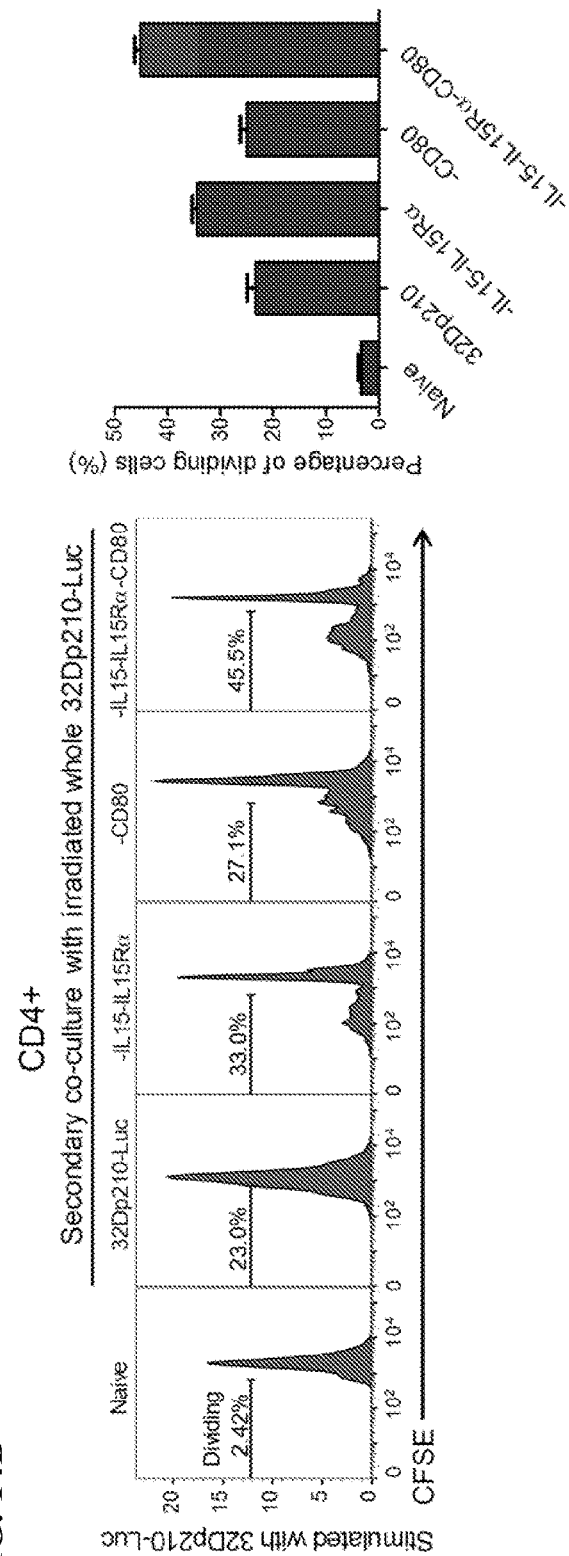

Example 8: In Vivo Administration of the 32Dp210-IL-15-IL-15Rα-CD80 Vaccine Stimulates Robust T Cell Proliferation and Cytolytic Activity The immunostimulatory effects of 32Dp210-based vaccines were first evaluated in vivo in normal, non-tumor bearing mice where leukemia-mediated stimulation of immune inhibitory cell types would not confound comparative analysis of immune responses. Normal C3H mice were injected SC with irradiated 32Dp210-CD80, 32Dp210-IL-15-IL15Rα, or 32Dp210-IL15-IL15Rα-CD80 vaccines, weekly for a month. Control groups included age-matched, un-injected C3H mice, and mice vaccinated with the irradiated, un-transduced 32Dp210 parent line. Thereafter, splenocytes were harvested, re-stimulated with 32Dp210 parent cells, and stained for flow cytometric analysis. Highest levels of CD3+CD8+ T cell proliferation were stimulated by 32Dp210-IL-15-IL-15Rα and 32Dp210-IL-15-IL-15Rα-CD80 vaccination (FIG. 14A). In the CD3+CD4+ T cell population from vaccinated mice, prior exposure to either of the IL-15-IL-15Rα expressing vaccines stimulated greatest proliferative responses (FIG. 14B).

Figure 4:
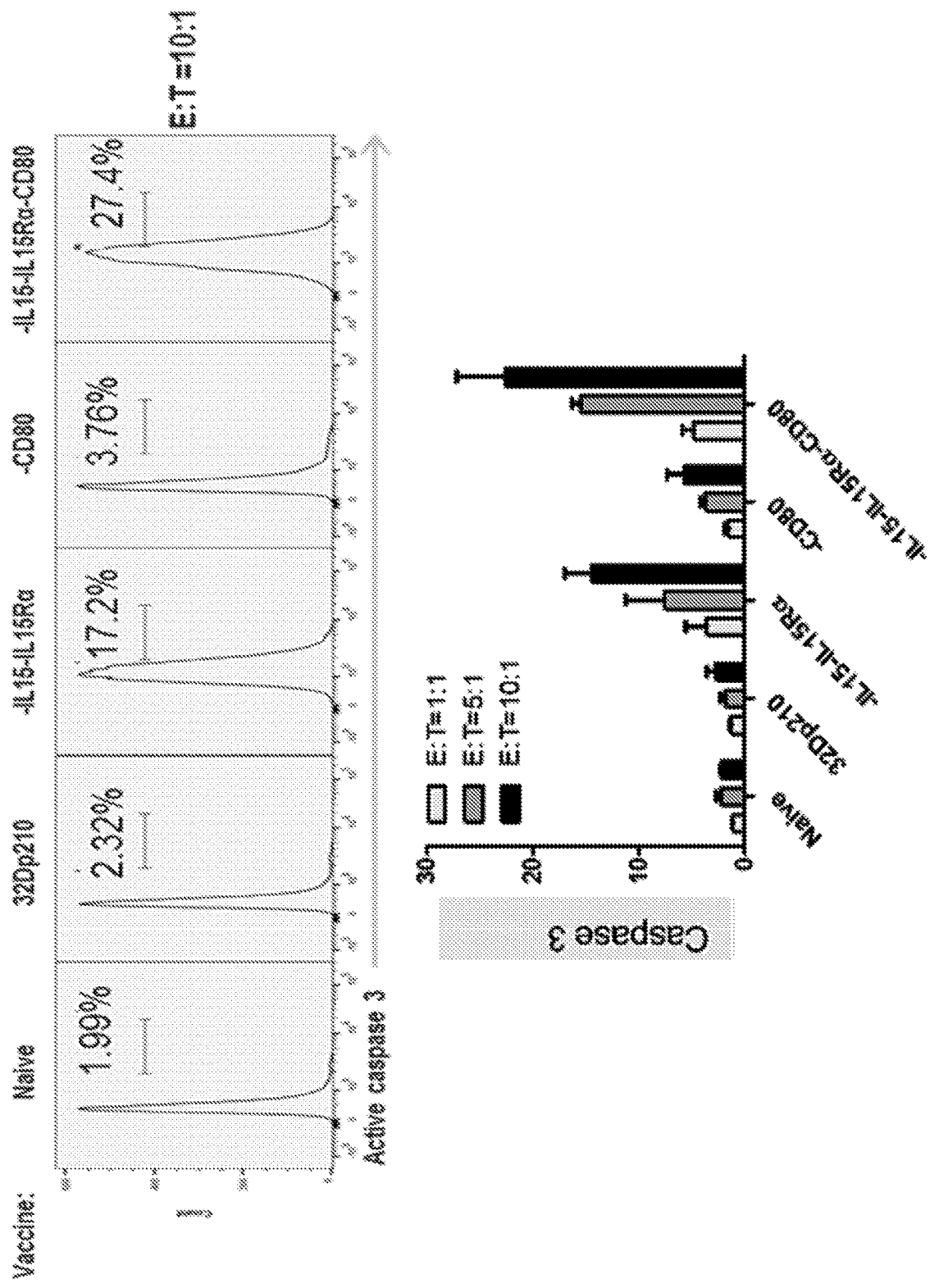
FIG. 4 shows graphs of a CTL assay of the splenocytes from C3H mice vaccinated with 32Dp210-luc whole cell vaccines.
Figure 5:
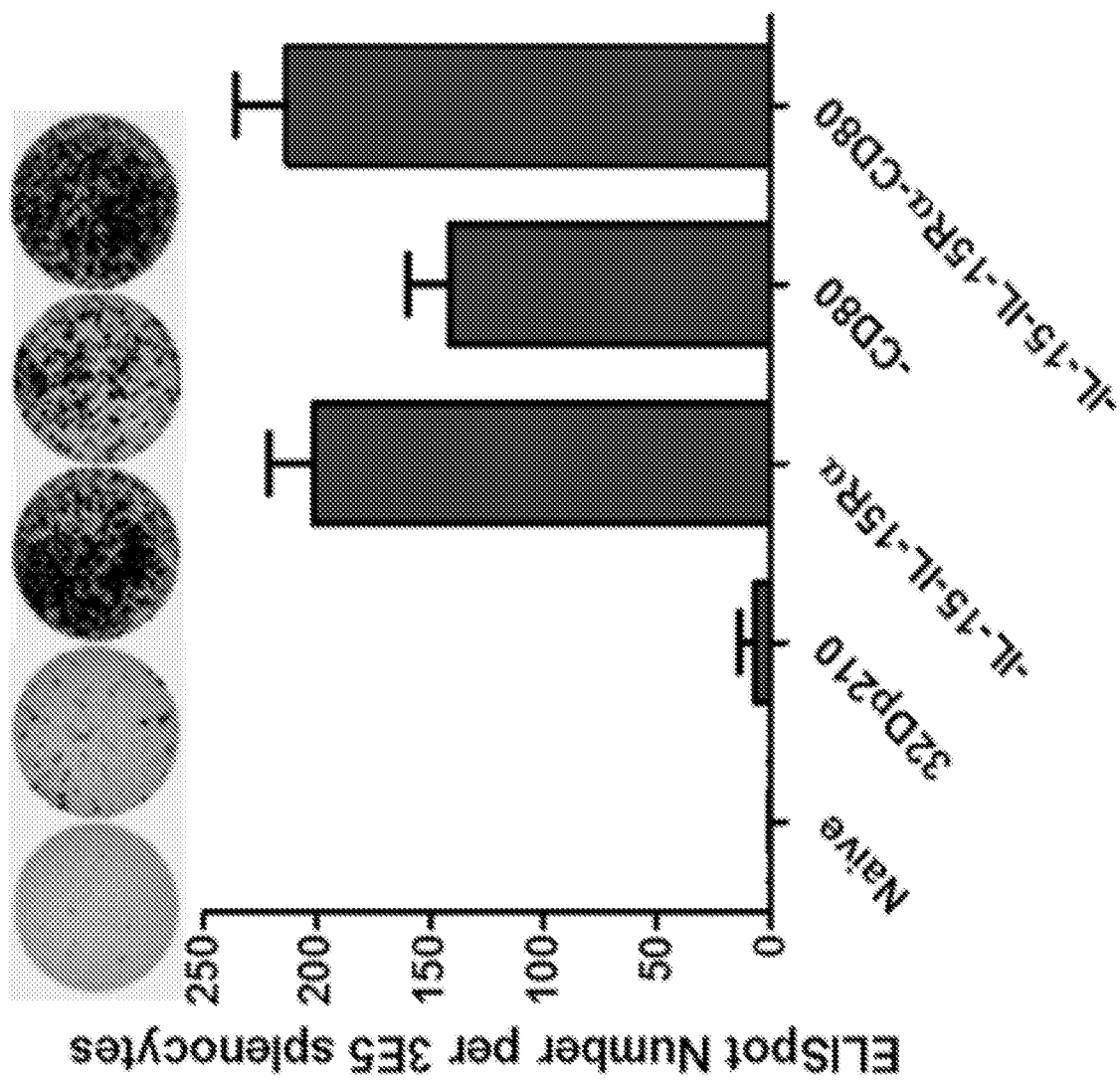
FIG. 5 is a graph of an ELISpot assay for IFN-γ secretion post vaccination.
Figure 15A:
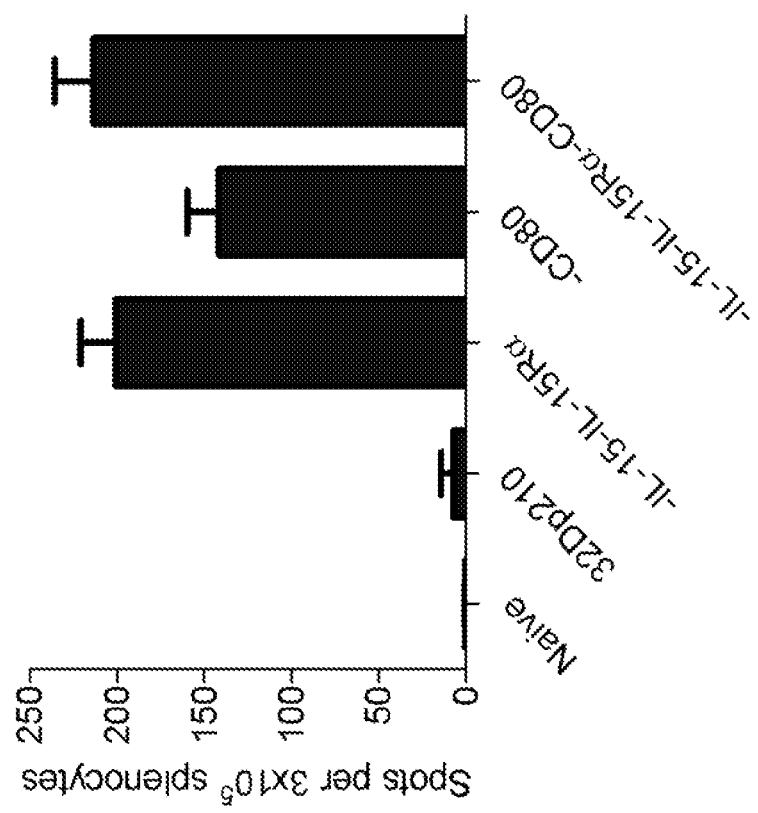
FIG. 15A-FIG. 15B depict splenocytes from C3H mice serially vaccinated with 32Dp210-derived whole cell vaccines have enhanced cytolytic activity ex vivo. After 4 weekly vaccinations with $2\times10^6$ irradiated 32Dp210-Luc, 32Dp210-mIL-15-IL-15Rα, 32Dp210-CD80, or 32Dp210-IL-15-IL-15Rα-CD80 cells, splenocytes were harvested, re-stimulated in vitro with irradiated (100Gy) 32Dp210 parent cells for 5 days. Splenocytes re-stimulated in vitro were then purified on a density gradient of Ficoll and used as effectors in ex vivo cytolytic assays.
Figure 15B:
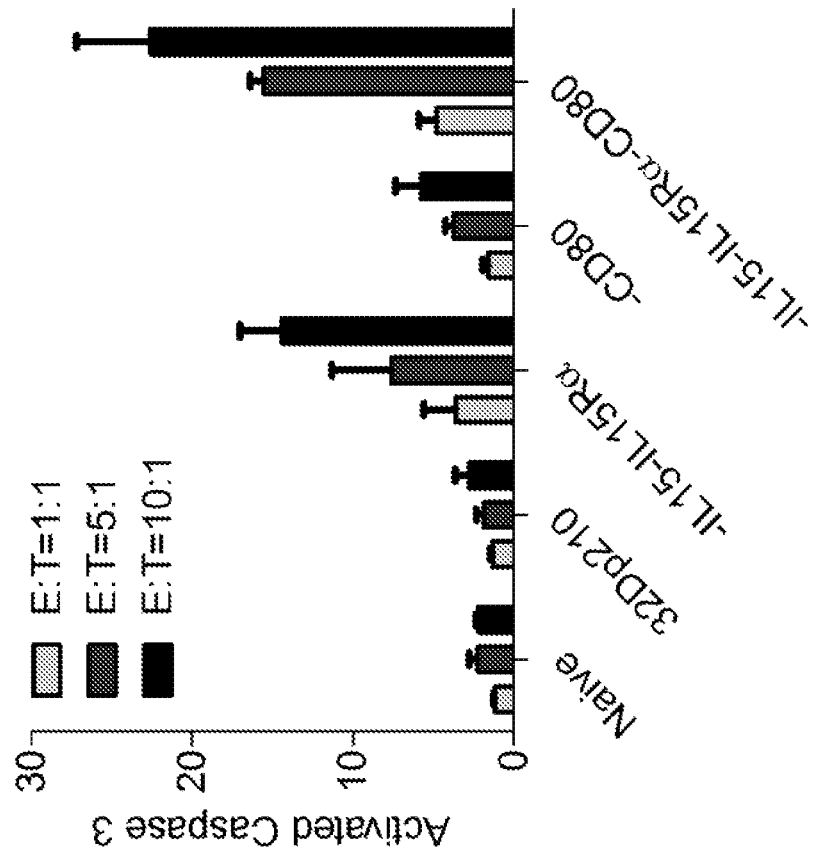

The anti-leukemic cytolytic activity by stimulated by 32Dp210-derived vaccines was tested in ex vivo assays. T cells from mice treated with the combination 32Dp210-IL-15-IL-15Rα-CD80 vaccine exhibited highest levels of cytolytic activity at all effector to target ratios, although 32Dp210-IL-15-IL-15Rα vaccination also stimulated significant cytolytic responses (FIG. 4 and FIG. 15A). Consistent with activation and expansion of cytotoxic T cells, increased frequencies of IFNγ-expressing cells were also observed after secondary stimulation of splenocytes from vaccinated non tumor-bearing mice (FIG. 5 and FIG. 15B). In parallel experiments, serially vaccinated normal mice were challenged IV with 32Dp210 leukemia after vaccination. Non-tumor-bearing mice treated with the 32Dp210-IL-15-IL-15Rα-CD80 vaccine had higher rates of survival (80%) in subsequent tumor challenge studies than did mice treated with 32Dp210-IL-15-IL-15Rα or 32Dp210-CD80 vaccines (25-50%). All mice that survived 100 days after their initial vaccination and subsequent tumor challenge were able to reject 32Dp210 leukemia after a second inoculation with 32Dp210 leukemia, 5 months after the initial vaccination. Thus, 32Dp210-derived vaccines can stimulate effective and long-lasting anti-leukemic immunity.

Figure 16A:
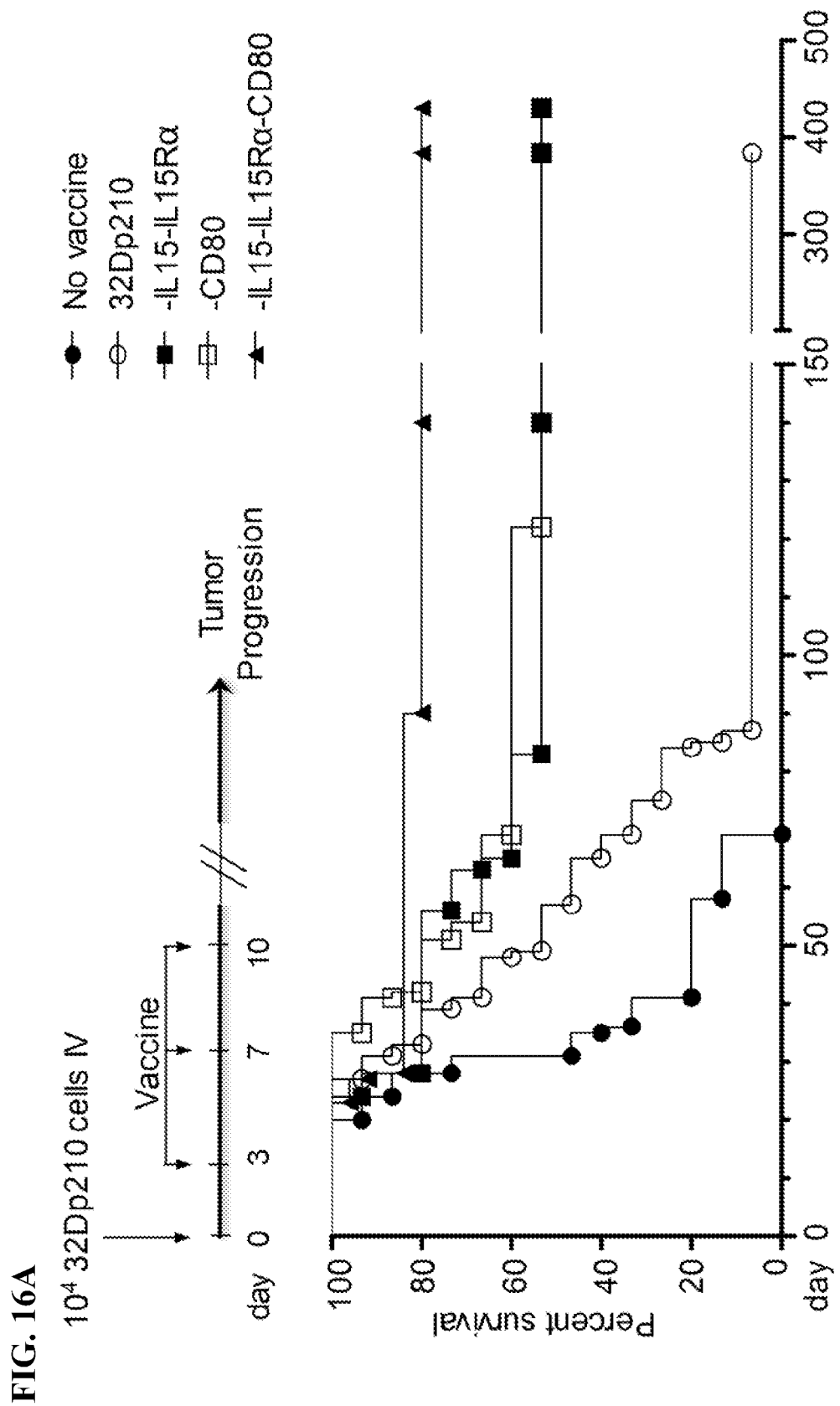
FIG. 16A-FIG. 16B depict administration of lentivirally engineered 32Dp210 vaccines enables greater progression free and overall survival in 32Dp210 leukemia bearing mice.

Example 9: In Vivo Administration of the 32Dp210-IL-15-IL-15Rα-CD80 Vaccine Stimulates Robust T Cell Proliferation and Cytolytic Activity The therapeutic efficacy of 32Dp210-derived vaccines administered to mice with established leukemia was then tested beginning three days after injection of 1×10⁴ 32Dp210 cells when leukemia is established in the bone marrow (FIG. 9). All of the leukemic mice in the unvaccinated control groups succumbed by day 70 with the majority succumbing at 30-40 days post tumor inoculum (FIG. 16A). Vaccination with parent 32Dp210 cells prolonged survival compared to un-vaccinated controls, consistent with previously described immunogenicity of irradiated tumor cells, but resulted in <10% survival[41,42]. Mice treated with 32Dp210-CD80, 32Dp210-IL-15-IL-15Rα, or 32Dp210-IL-15-IL-15Rα-CD80 all exhibited greater long-term survival than did mice vaccinated with the parental 32Dp210 cells (FIG. 16A). Remarkably, leukemic mice treated with the combination 32Dp210-IL-15-IL-15Rα-CD80 vaccine had overall survival rates approaching 80%. Thus, combining co-stimulation by CD80, and immune stimulation by IL-15-IL-15Rα, induces effective anti-leukemic activity, even in the context of leukemia-associated stimulation of inhibitory immune effectors. When 32Dp210-IL-15-IL-15Rα-CD80 vaccinated leukemic mice in remission were re-challenged with 32Dp210 inoculation, all subjects rejected the tumor.

Figure 6:
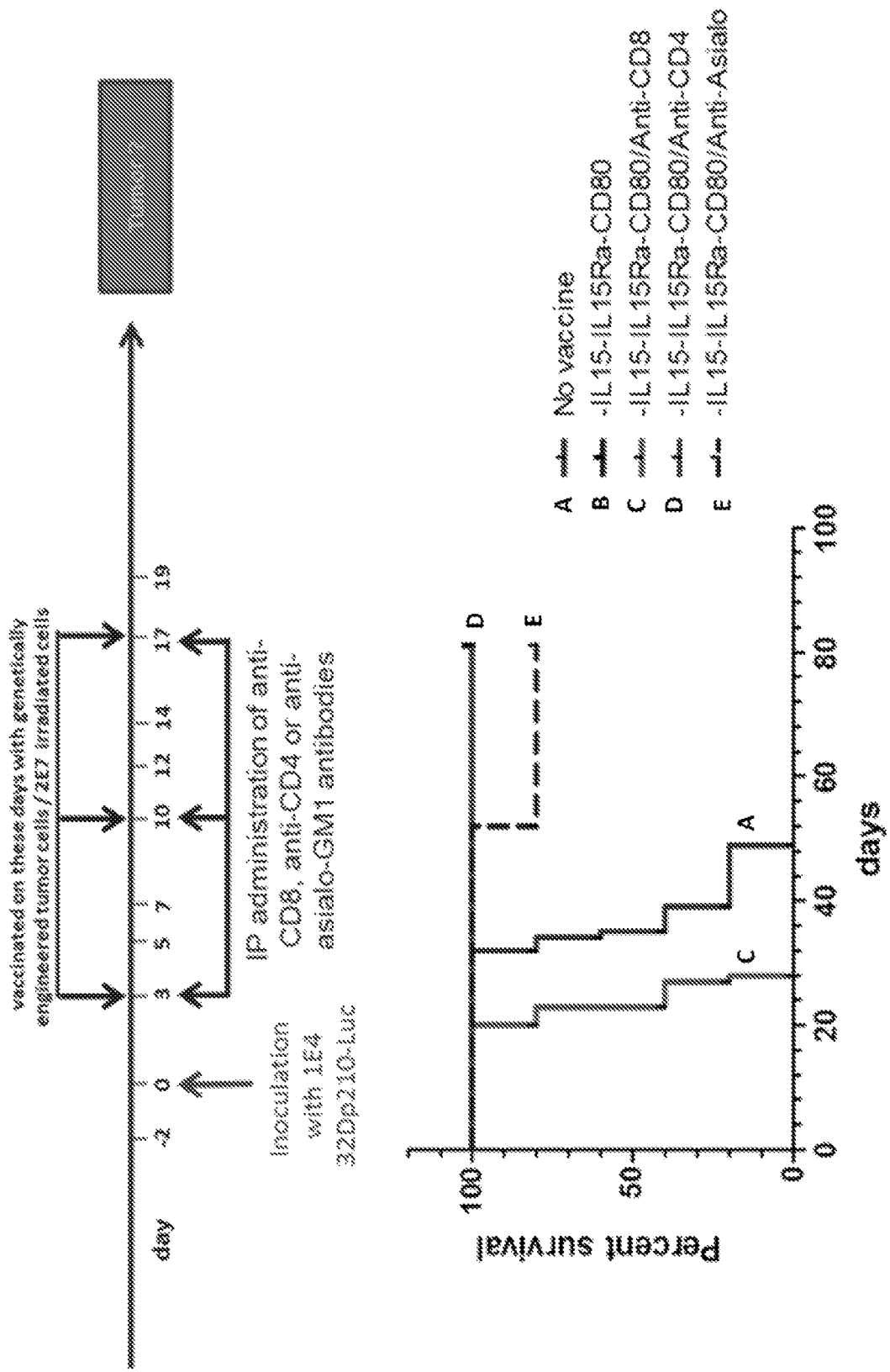
FIG. 6 is a graph of in vivo depletion studies in leukemic C3H mice vaccinated with 32Dp210-IL15-IL15Ra-CD80 whole cell vaccines.
Figure 16B:
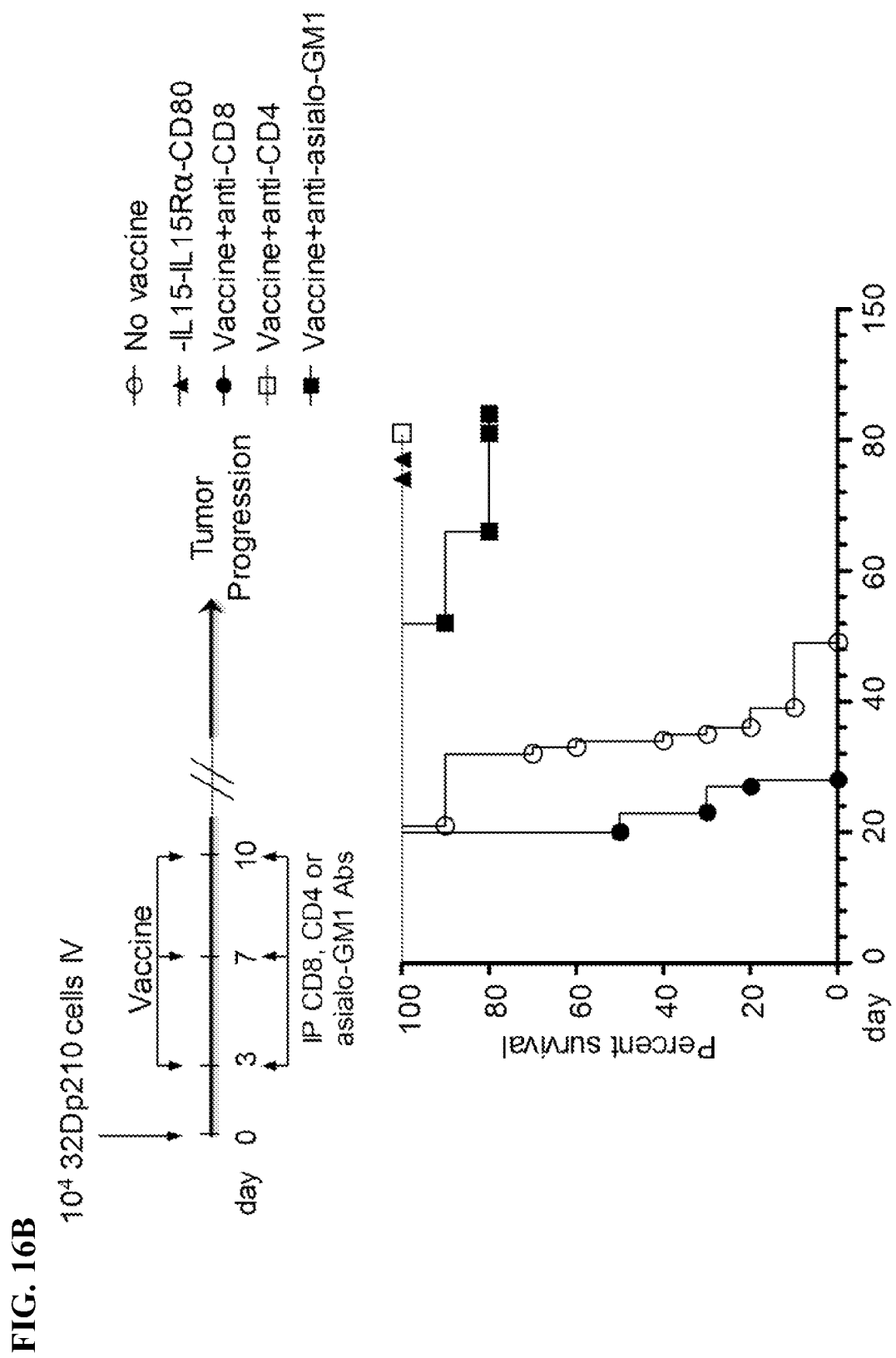

Example 10: In Vivo Depletion of CD8+ Populations Abrogates 32Dp210-IL-15-IL-15Rα-CD80 Vaccine Efficacy To begin to define the immune effectors involved in leukemia-specific responses, we performed in vivo antibody-mediated depletion studies with either anti-CD4, or anti-CD8 antibodies, or with the anti-asialo-GM1 antibody (AS-GM1) to deplete NK cells. The AS-GM1 antibody, which binds to NK cells and also to some activated T cells[43,44] and to basophils[45] was used instead of anti-NK1.1 antibody, as the NK1.1 antigen (CD161b/CD161c) is not expressed in C3H mice[46,47]. Antibody administration, produced >90% depletion of target cells in peripheral blood, as shown by flow cytometric analysis one day after injection. Treatment with anti-CD4+ or anti-AS-GM1 anti-bodies, had minimal effects on vaccine outcomes; however, depletion of CD8+ cells completely abrogated the effects of 32Dp210-IL-15-IL-15Rα-CD80 vaccination on survival, indicating that the anti-leukemic effects of this vaccine are primarily mediated by CD8+ T cells. (FIG. 6 and FIG. 16B).

Example 11: Treatment with the 32Dp210-IL-15-IL-15Rα-CD80 Vaccine Shows Efficacy in a Murine Model of Post-Remission MRD The major clinical application of an autologous AML vaccine strategy would be as post-remission immunotherapy to prolong relapse free survival in patients with MRD. To recapitulate this clinical setting, we developed a murine model of MRD for testing our vaccine. Initially, several chemotherapeutic regimens, previously shown to induce transient responses in 32Dp210 leukemia, were tested[48]. However, advanced 32Dp210 leukemia proved to be highly chemo-refractory. Dose-finding studies with either cytosine arabinoside (AraC), and/or high dose Dasatinib to target the bcr-abl tyrosine kinase in 32Dp210 leukemia, were either ineffective, or resulted in both toxicity and lethality in leukemic mice (data not shown). A different strategy was therefore adopted for achieving post-remission MRD in mice with high leukemia burdens by lentivirally engineering a 32Dp210 cell line to express the herpes thymidine kinase (HSV-TK) suicide gene[36]. Using this approach, treatment with ganciclovir (GCV) could be used to induce remission without the confounding immune and cytopenic effects of conventional chemotherapy[49]. In this context, GCV treatment should not have a direct impact on leukemia-associated immune deviation, except as associated with reduction of tumor burden, since effects of GCV are primarily restricted to suppression of marrow proliferation, but not inhibition of immune function[50]. Analysis of blood samples from mice after 2 weeks of treatment with GCV confirmed that there was no significant decline in WBC, neutrophils, hemoglobin, or monocytes, and only a small reduction in the number of peripheral lymphocytes that remained within the normal range (Table 1).

TABLE 1

Effect of GCV on CBC

| (k/μL) | PBS | GCV | P-value |
|---|---|---|---|
| White Blood Cells | 8.512 ± 0.610 | 6.638 ± 0.575 | 0.064 |
| Neutrophils | 4.068 ± 0.568 | 4.141 ± 0.580 | 0.938 |
| Lymphocytes | 3.682 ± 0.208 | 2.036 ± 0.279 | 0.002 |
| Monocytes | 0.5100 ± 0.077 | 0.310 ± 0.0364 | 0.018 |

Figure 17A:
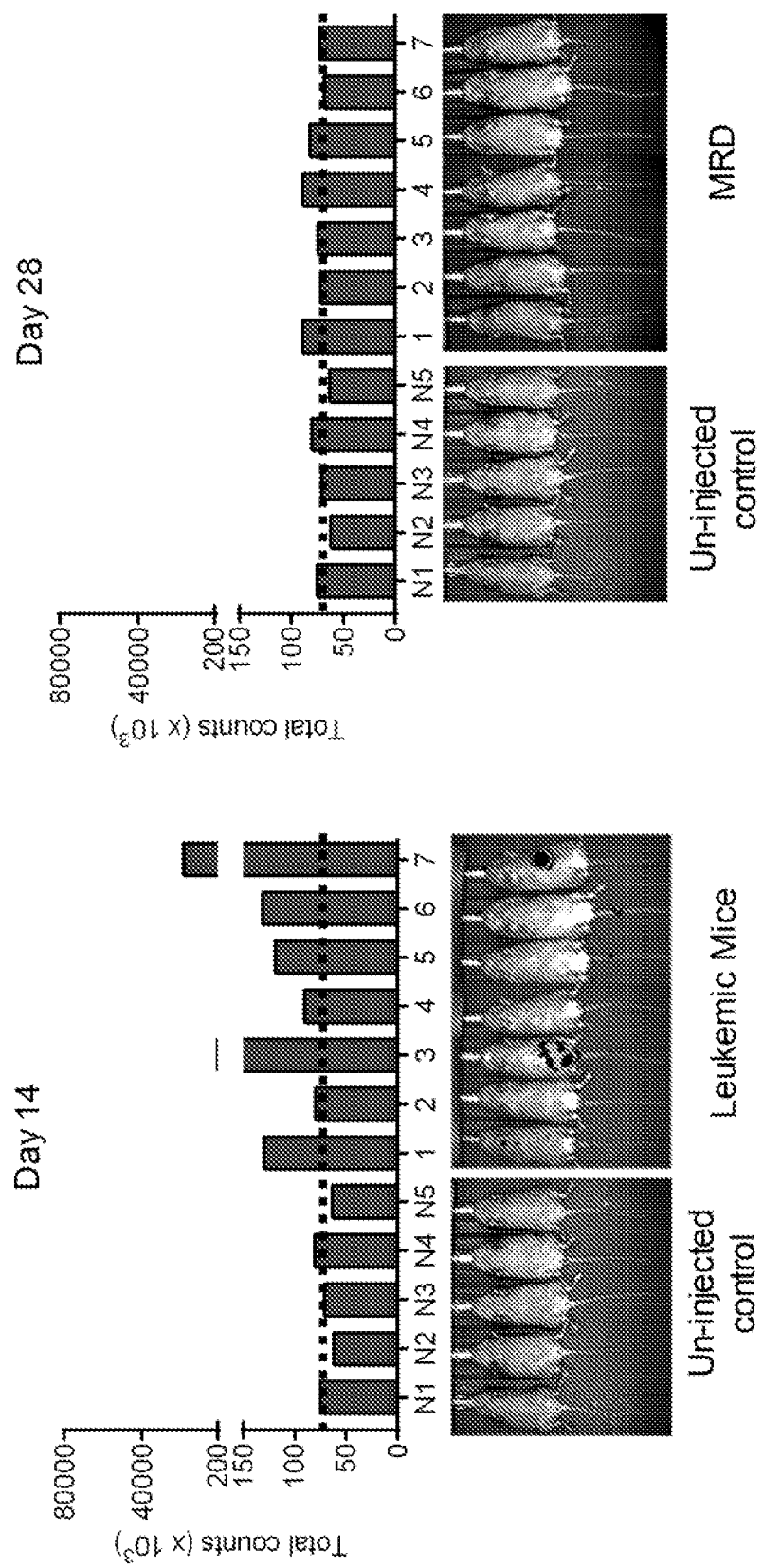
FIG. 17A-FIG. 17C depict development of a minimal residual diseased (MRD) model in 32Dp210 leukemia.
Figure 17B:
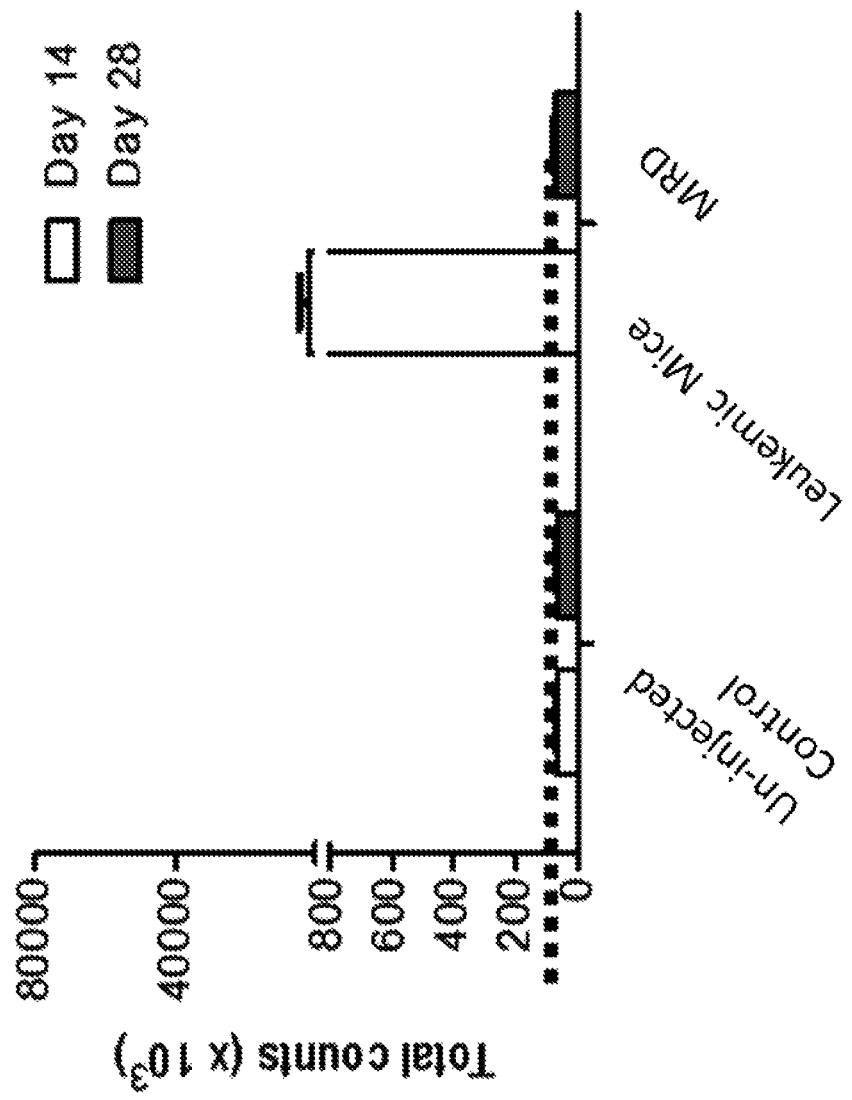
Figure 17C:
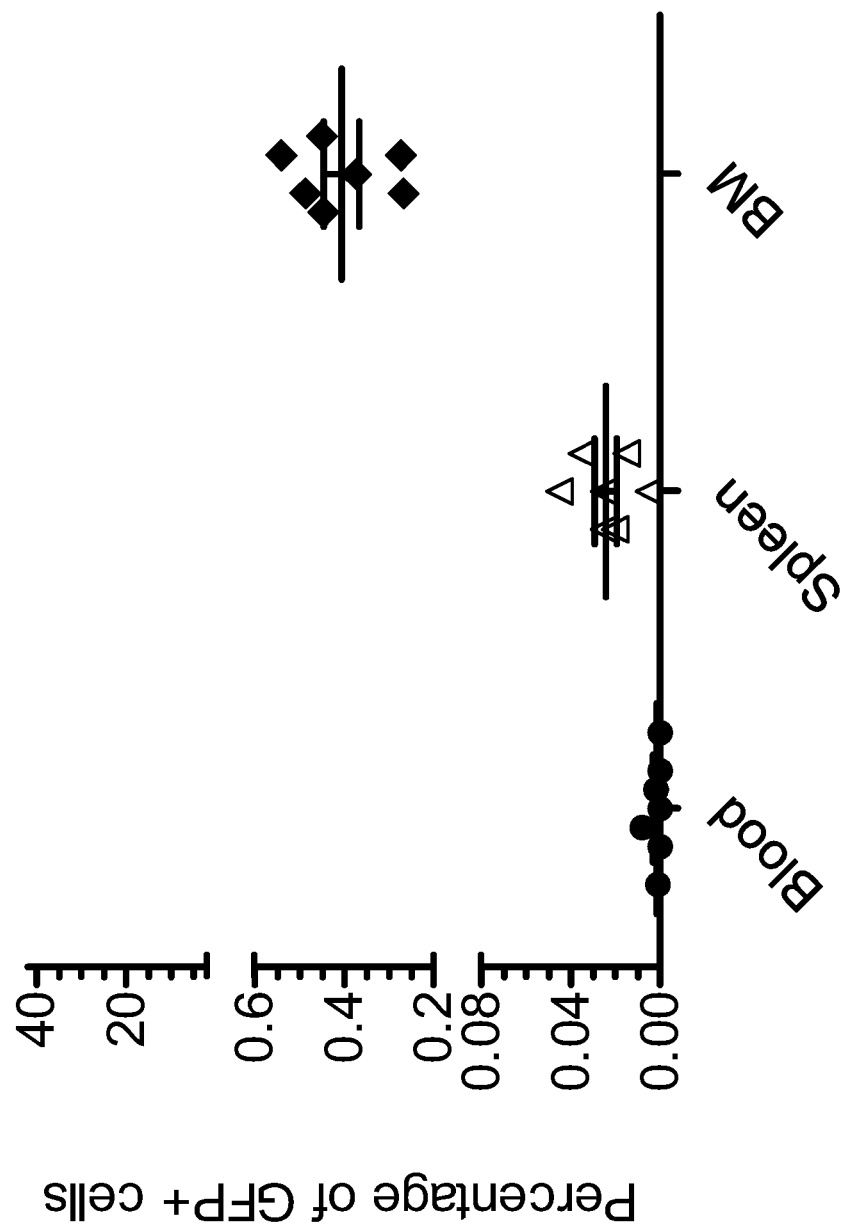

To validate this model, mice were treated daily with GCV once 32Dp210 leukemia was evident by IVIS. Although expression of HSV-TK, has been reported to be immunogenic in some studies[51], HSV-TK expression in 32Dp210 cells did not affect either the rate of leukemic engraftment, or progression of disease (FIG. 17). Remission was arbitrarily defined as a level of bioluminescence comparable to background levels in age-matched, luciferin-injected normal mice. (FIG. 17A). Seven of 10 mice that began GCV treatment on day 14 after tumor inoculation showed remission two weeks later (day 28). Prior to initiation of GCV treatment, the average leukemic burdens in mice before therapy Day 14, were comparable (FIG. 17B). To assess responses after GCV treatment, the frequency of 32Dp210-GFP+/HSV-TK+ cells in spleen, blood, and bone marrow were quantified by flow cytometric analysis (FIG. 17C). Analysis showed that all GCV-treated leukemic mice with background levels of in vivo bioluminescence and by definition, clinical remission, with pathological remission (<5% blasts in bone marrow), had persistence of MRD (<0.5% GFP+ cells in BM (n=7/7)) (FIG. 17C). Lower numbers of GFP+ leukemia cells were detected in spleen after 14 days of GCV.

Figure 18A:
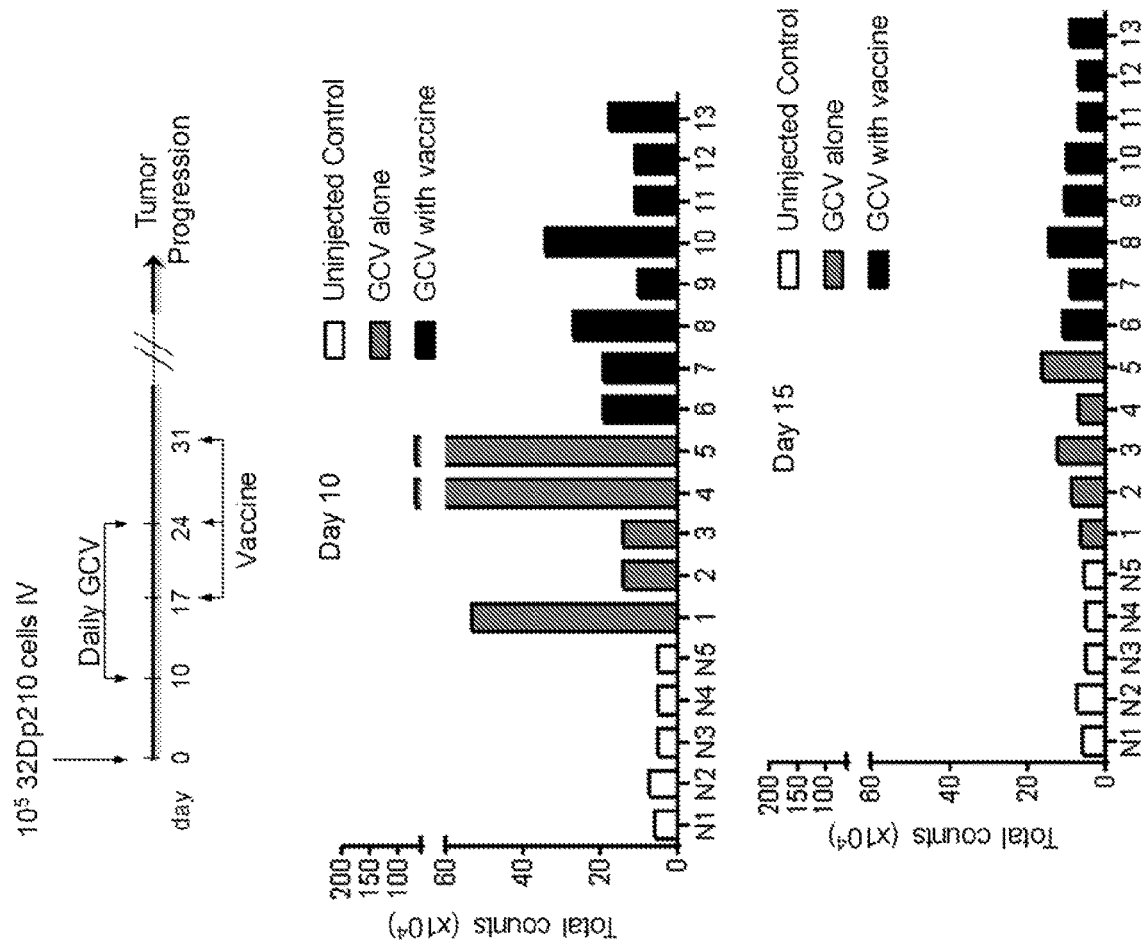
FIG. 18A-FIG. 18B depict the efficacy of the 32Dp210 vaccine as post-remission therapy to treat MRD.
Figure 18B:
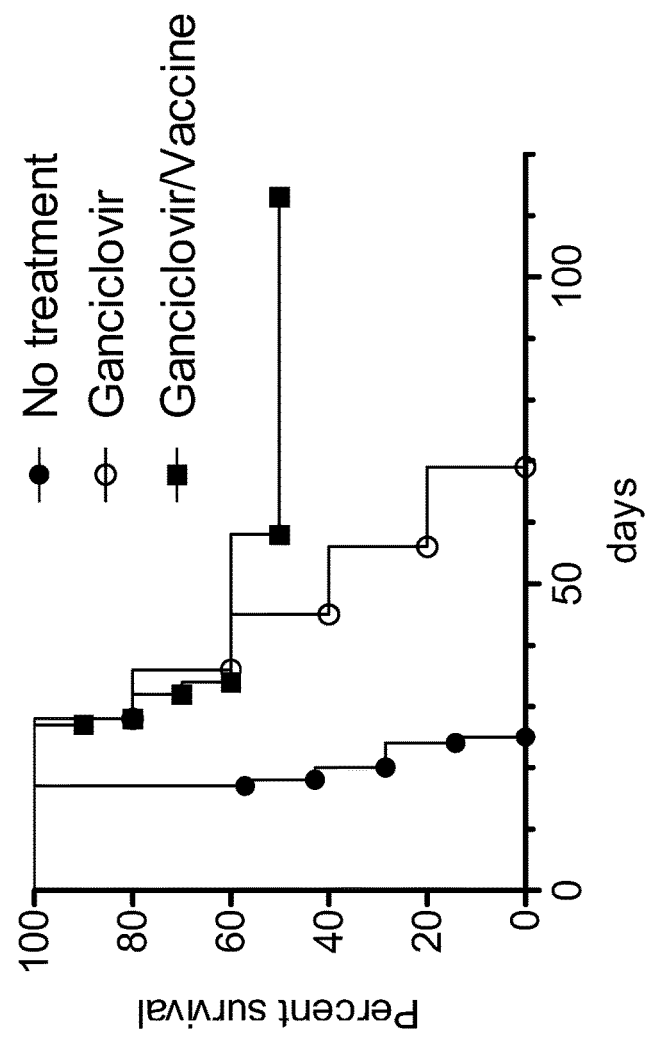

The efficacy of post-remission treatment with the 32Dp210-IL-15-IL-15Rα-CD80 vaccine was then tested in mice with established tumor burdens. A 10-fold larger dose of leukemic cells (1×10$^5$) 32Dp210-luc-HSV-TK+ cells) was administered to ensure that all mice had evidence of leukemia by IVIS on day 10, when GCV treatment was initiated in these mice (FIG. 18A, upper panel). By day 5 of GCV administration (day 15), most of the leukemic mice had major responses (FIG. 18A, lower panel). All animals that achieved remission with 14-day GCV and with no further therapy eventually relapsed; however, post-remission treatment with the 32Dp210-IL-15-IL-15Rα-CD80 vaccine improved progression-free survival, and controlled or eliminated MRD in 50% of mice, despite the persistence of leukemia-mediated inhibitory effects on host immunity (FIG. 18B).

REFERENCES

1. Dombret H, Gardin C. An update of current treatments for adult acute myeloid leukemia. Blood 2016; 127:53-61.
2. Rashidi A, Walter R B. Antigen-specific immunotherapy for acute myeloid leukemia: where are we now, and where do we go from here? Expert review of hematology 2016; 9:335-50.
3. Grosso D A, Hess R C, Weiss M A. Immunotherapy in acute myeloid leukemia. Cancer 2015; 121:2689-704.
4. Di Stasi A, Jimenez A M, Minagawa K, Al-Obaidi M, Rezvani K. Review of the Results of WT1 Peptide Vaccination Strategies for Myelodysplastic Syndromes and Acute Myeloid Leukemia from Nine Different Studies. Front Immunol 2015; 6:36.
5. Sasine J P, Schiller G J. Emerging strategies for high-risk and relapsed/refractory acute myeloid leukemia: novel agents and approaches currently in clinical trials. Blood Rev 2015; 29:1-9.
6. Borrello I M, Levitsky H I, Stock W, et al. Granulocyte-macrophage colony-stimulating factor (GM-CSF)-secreting cellular immunotherapy in combination with autologous stem cell transplantation (ASCT) as postremission therapy for acute myeloid leukemia (AML). Blood 2009; 114:1736-45.
7. Hardwick N, Chan L, Ingram W, Mufti G, Farzaneh F. Lytic activity against primary AML cells is stimulated in vitro by an autologous whole cell vaccine expressing IL-2 and CD80. Cancer Immunol Immunother 2010; 59:379-88.
8. Ingram W, Chan L, Guven H, et al. Human CD80/IL2 lentivirus-transduced acute myeloid leukaemia (AML) cells promote natural killer (NK) cell activation and cytolytic activity: implications for a phase I clinical study. Br J Haematol 2009; 145:749-60.
9. Teague R M, Kline J. Immune evasion in acute myeloid leukemia: current concepts and future directions. Journal for immunotherapy of cancer 2013; 1.
10. Posnett D N, Sinha R, Kabak S, Russo C. Clonal populations of T cells in normal elderly humans: the T cell equivalent to "benign monoclonal gammapathy". J Exp Med 1994; 179:609-18.
11. Hadrup S R, Strindhall J, Kollgaard T, et al. Longitudinal studies of clonally expanded CD8 T cells reveal a repertoire shrinkage predicting mortality and an increased number of dysfunctional cytomegalovirus-specific T cells in the very elderly. J Immunol 2006; 176:2645-53.
12. Mocchegiani E, Malavolta M. NK and NKT cell functions in immunosenescence. Aging cell 2004; 3:177-84.
13. Gravekamp C. The impact of aging on cancer vaccination. Curr Opin Immunol 2011; 23:555-60.
14. Boyer M W V D, Taylor P A, Gray G S, Katsanis E, Gorden K, Orchard P J, Blazar B R. The role of B7 costimulation by murine acute myeloid leukemia in the generation and function of a CD8+ T-cell line with potent in vivo graft-versus-leukemia properties. Blood 1997; 89:3477-85.
15. Koya R C, Kasahara N, Pullarkat V, Levine A M, Stripecke R. Transduction of acute myeloid leukemia cells with third generation self-inactivating lentiviral vectors expressing CD80 and GM-CSF: effects on proliferation, differentiation, and stimulation of allogeneic and autologous anti-leukemia immune responses. Leukemia 2002; 16:1645-54.
16. Anderson D M, Kumaki S, Ahdieh M, et al. Functional characterization of the human interleukin-15 receptor alpha chain and close linkage of IL15RA and IL2RA genes. The Journal of biological chemistry 1995; 270: 29862-9.
17. Bergamaschi C, Rosati M, Jalah R, et al. Intracellular interaction of interleukin-15 with its receptor alpha during production leads to mutual stabilization and increased bioactivity. The Journal of biological chemistry 2008; 283:4189-99.
18. Sandau M M, Schluns K S, Lefrancois L, Jameson S C. Cutting edge: transpresentation of IL-15 by bone marrow-derived cells necessitates expression of IL-15 and IL-15R alpha by the same cells. J Immunol 2004; 173:6537-41.
19. Stoklasek T A, Schluns K S, Lefrancois L. Combined IL-15/IL-15Ralpha immunotherapy maximizes IL-15 activity in vivo. J Immunol 2006; 177:6072-80.
20. Mortier E, Woo T, Advincula R, Gozalo S, Ma A. IL-15Ralpha chaperones IL-15 to stable dendritic cell membrane complexes that activate NK cells via trans presentation. J Exp Med 2008; 205:1213-25.
21. Rosati M, Valentin A, Jalah R, et al. Increased immune responses in rhesus macaques by DNA vaccination combined with electroporation. Vaccine 2008; 26:5223-9.
22. Bergamaschi C, Jalah R, Kulkarni V, et al. Secretion and biological activity of short signal peptide IL-15 is chaperoned by IL-15 receptor alpha in vivo. J Immunol 2009; 183:3064-72.
23. Waldmann T A. The shared and contrasting roles of IL2 and IL15 in the life and death of normal and neoplastic lymphocytes: implications for cancer therapy. Cancer immunology research 2015; 3:219-27.
24. Bergamaschi C, Bear J, Rosati M, et al. Circulating IL-15 exists as heterodimeric complex with soluble IL-15Ralpha in human and mouse serum. Blood 2012; 120: e1-8.
25. Chertova E, Bergamaschi C, Chertov O, et al. Characterization and favorable in vivo properties of heterodimeric soluble IL-15. IL-15Ralpha cytokine compared to IL-15 monomer. The Journal of biological chemistry 2013; 288:18093-103.
26. Waldmann T A, Lugli E, Roederer M, et al. Safety (toxicity), pharmacokinetics, immunogenicity, and impact on elements of the normal immune system of recombinant human IL-15 in rhesus macaques. Blood 2011; 117:4787-95.
27. Daley G Q, Van Etten R A, Baltimore D. Induction of chronic myelogenous leukemia in mice by the P210bcr/abl gene of the Philadelphia chromosome. Science 1990; 247:824-30.
28. Van den Bergh J, Willemen Y, Lion E, et al. Transpresentation of interleukin-15 by IL-15/IL-15Ralpha mRNA-engineered human dendritic cells boosts antitumoral natural killer cell activity. Oncotarget 2015; 6:44123-33.
29. Sun H, Liu D. IL-15/sIL-15Ralpha gene transfer suppresses Lewis lung cancer growth in the lungs, liver and kidneys. Cancer Gene Ther 2016; 23:54-60.
30. Romano E, Cotari J W, Barreira da Silva R, et al. Human Langerhans cells use an IL-15R-alpha/IL-15/pSTAT5-dependent mechanism to break T-cell tolerance against the self-differentiation tumor antigen WT1. Blood 2012; 119:5182-90.
31. Matulonis U, Salgia R, Okuda K, Druker B, Griffin J D. Interleukin-3 and p210 BCR/ABL activate both unique and overlapping pathways of signal transduction in a factor-dependent myeloid cell line. Exp Hematol 1993; 21:1460-6.
32. Chan L, Hardwick N, Darling D, et al. IL-2/B7.1 (CD80) fusagene transduction of AML blasts by a self-inactivating lentiviral vector stimulates T cell responses in vitro: a strategy to generate whole cell vaccines for AML. Mol Ther 2005; 11:120-31.
33. Jalah R, Rosati M, Kulkarni V, et al. Efficient systemic expression of bioactive IL-15 in mice upon delivery of optimized DNA expression plasmids. DNA and cell biology 2007; 26:827-40.
34. Kim J H, Lee S R, Li L H, et al. High cleavage efficiency of a 2A peptide derived from porcine teschovirus-1 in human cell lines, zebrafish and mice. PLoS One 2011; 6: e18556.
35. Donnelly M L, Hughes L E, Luke G, et al. The 'cleavage' activities of foot-and-mouth disease virus 2A site-directed mutants and naturally occurring '2A-like' sequences. J Gen Virol 2001; 82:1027-41.
36. Falahati R, Zhang J, Flebbe-Rehwaldt L, Shi Y, Gerson S L, Gaensler K M. Chemoselection of allogeneic HSC after murine neonatal transplantation without myeloablation or post-transplant immunosuppression. Mol Ther 2012; 20:2180-9.
37. Plebanski M, Katsara M, Sheng K C, Xiang S D, Apostolopoulos V. Methods to measure T-cell responses. Expert Rev Vaccines 2010; 9:595-600.
38. Cook G J, Pardee T S. Animal models of leukemia: any closer to the real thing? Cancer metastasis reviews 2013; 32:63-76.
39. Sweeney C L, Frandsen J L, Verfaillie C M, McIvor R S. Trimetrexate inhibits progression of the murine 32Dp210 model of chronic myeloid leukemia in animals expressing drug-resistant dihydrofolate reductase. Cancer Res 2003; 63:1304-10.
40. Vallera D A, Seo S Y, Panoskaltsis-Mortari A, Griffin J D, Blazar B R. Targeting myeloid leukemia with a DT(390)-mIL-3 fusion immunotoxin: ex vivo and in vivo studies in mice. Protein engineering 1999; 12:779-85.
41. Ciernik I F, Romero P, Berzofsky J A, Carbone D P. Ionizing radiation enhances immunogenicity of cells expressing a tumor-specific T-cell epitope. International journal of radiation oncology, biology, physics 1999; 45:735-41.
42. Dranoff G, Jaffee E, Lazenby A, et al. Vaccination with irradiated tumor cells engineered to secrete murine granulocyte-macrophage colony-stimulating factor stimulates potent, specific, and long-lasting anti-tumor immunity. Proc Natl Acad Sci USA 1993; 90:3539-43.
43. Slifka M K, Pagarigan R R, Whitton J L. NK markers are expressed on a high percentage of virus-specific CD8+ and CD4+ T cells. J Immunol 2000; 164:2009-15.
44. Stitz L, Baenziger J, Pircher H, Hengartner H, Zinkernagel R M. Effect of rabbit anti-asialo GM1 treatment in vivo or with anti-asialo GM1 plus complement in vitro on cytotoxic T cell activities. J Immunol 1986; 136:4674-80.
45. Nishikado H, Mukai K, Kawano Y, Minegishi Y, Karasuyama H. NK cell-depleting anti-asialo GM1 antibody exhibits a lethal off-target effect on basophils in vivo. J Immunol 2011; 186:5766-71.
46. Giorda R, Weisberg E P, Ip T K, Trucco M. Genomic structure and strain-specific expression of the natural killer cell receptor NKR-P1. J Immunol 1992; 149:1957-63.
47. Carlyle J R, Mesci A, Ljutic B, et al. Molecular and genetic basis for strain-dependent NK1.1 alloreactivity of mouse NK cells. J Immunol 2006; 176:7511-24.
48. Sweeney C L, Diers M D, Frandsen J L, Gunther R, Verfaillie C M, McIvor R S. Methotrexate exacerbates tumor progression in a murine model of chronic myeloid leukemia. The Journal of pharmacology and experimental therapeutics 2002; 300:1075-84.
49. Rivas C, Miller A R, Collado M, Lam E W, Apperley J F, Melo J V. BCR-ABL-expressing cells transduced with the HSV-tk gene die by apoptosis upon treatment with ganciclovir. Mol Ther 2001; 3:642-52.
50. McGavin J K, Goa K L. Ganciclovir: an update of its use in the prevention of cytomegalovirus infection and disease in transplant recipients. Drugs 2001; 61:1153-83.
51. Berger C, Flowers M E, Warren E H, Riddell S R. Analysis of transgene-specific immune responses that limit the in vivo persistence of adoptively transferred HSV-TK-modified donor T cells after allogeneic hematopoietic cell transplantation. Blood 2006; 107:2294-302.
52. Xu W, Jones M, Liu B, et al. Efficacy and mechanism-of-action of a novel superagonist interleukin-15: interleukin-15 receptor alphaSu/Fc fusion complex in syngeneic murine models of multiple myeloma. Cancer Res 2013; 73:3075-86.
53. Zhang M, Ju W, Yao Z, et al. Augmented IL-15Ralpha expression by CD40 activation is critical in synergistic CD8 T cell-mediated antitumor activity of anti-CD40 antibody with IL-15 in TRAMP-C2 tumors in mice. J Immunol 2012; 188:6156-64.
54. Dubois S, Mariner J, Waldmann T A, Tagaya Y. IL-15Ralpha recycles and presents IL-15 In trans to neighboring cells. Immunity 2002; 17:537-47.
55. Bessard A, Sole V, Bouchaud G, Quemener A, Jacques Y. High antitumor activity of RLI, an interleukin-15 (IL-15)-IL-15 receptor alpha fusion protein, in metastatic melanoma and colorectal cancer. Mol Cancer Ther 2009; 8:2736-45.
56. Hong E, Usiskin I M, Bergamaschi C, et al. Configuration-dependent Presentation of Multivalent IL-15: IL-15Ralpha Enhances the Antigen-specific T Cell Response and Anti-tumor Immunity. The Journal of biological chemistry 2016; 291:8931-50.
57. Gillgrass A. G N, Babian A. and Ashkar A A. The Absence or Overexpression of IL-15 Drastically Alters Breast Cancer Metastasis via Effects on NK Cells, CD4 T Cells, and Macrophages. J Immunol 2014.
58. Hasan A N, Selvakumar A, Shabrova E, et al. Soluble and membrane bound IL-15 Ralpha/IL-15 complexes mediate proliferation of high avidity central memory CD8 T-cells for adoptive immunotherapy of cancer and infections. Clin Exp Immunol 2016.
59. Di Carlo E, Comes A, Basso S, et al. The combined action of IL-15 and IL-12 gene transfer can induce tumor cell rejection without T and NK cell involvement. J Immunol 2000; 165:3111-8.
60. Comes A, Di Carlo E, Musiani P, et al. IFN-gamma-independent synergistic effects of IL-12 and IL-15 induce anti-tumor immune responses in syngeneic mice. Eur J Immunol 2002; 32:1914-23.
61. Kishida T, Asada H, Itokawa Y, et al. Electrochemo-gene therapy of cancer: intratumoral delivery of interleukin-12 gene and bleomycin synergistically induced therapeutic immunity and suppressed subcutaneous and metastatic melanomas in mice. Mol Ther 2003; 8:738-45.
62. Kowalczyk A, Wierzbicki A, Gil M, et al. Induction of protective immune responses against NXS2 neuroblastoma challenge in mice by immunotherapy with GD2 mimotope vaccine and IL-15 and IL-21 gene delivery. Cancer Immunol Immunother 2007; 56:1443-58.
63. Hu J, Oda S K, Shotts K, et al. Lysophosphatidic acid receptor 5 inhibits B cell antigen receptor signaling and antibody response. J Immunol 2014; 193:85-95.
64. Mehta R S, Chen X, Antony J, Boyiadzis M, Szabolcs P. Generating Peripheral Blood Derived Lymphocytes Reacting Against Autologous Primary AML Blasts. J Immunother 2016; 39:71-80.

What is claimed is:

1. A cell media composition comprising:
   (1) recombinant leukemia cells comprising a multicistronic nucleic acid molecule comprising nucleic acid sequences encoding IL-15, IL-15Rα, and CD80,
      wherein the sequences encoding IL-15, IL-15Rα, and CD80 are linked to one another via a self-cleaving peptide sequence,
      wherein the recombinant leukemia cells are capable of: (i) expressing IL-15, IL-15Rα, and CD80 on the cell surface; and (ii) secreting IL-15 from said cells into the media; and
   (2) IL-15 secreted from the recombinant leukemia cells, wherein the concentration of secreted IL-15 in the cell media composition is about 150-400 ng/mL.

2. The media composition of claim 1, wherein the recombinant leukemia cells are acute myelogenous leukemia (AML) cells.

3. The media composition of claim 1, wherein the recombinant leukemia cell are derived from an individual diagnosed with or thought to have leukemia.

4. The media composition of claim 3, wherein the individual is in remission for AML.

5. The media composition of claim 4, wherein the individual is with AML in remission with minimal residual disease (MRD).

6. The media composition of claim 1, wherein the composition is irradiated.

7. The media composition of claim 1, wherein the recombinant leukemia cells are created by transduction with a vector comprising the multicistronic nucleic acid molecule.

8. A method of stimulating an immune response in an individual with acute myelogenous leukemia (AML) in remission with persistent minimal residual disease (MRD), comprising administering an effective amount of a cell media composition according to claim 1.

9. The method of claim 8, wherein the recombinant leukemia cells are autologous cells derived from the individual.

10. The method of claim 8, wherein the composition is formulated into a whole-cell vaccine.

11. The method of claim 8, wherein the method
   (i) stimulates the proliferation of one or more of CD3+ CD8$^+$ T cells, CD3$^+$CD4$^+$ T cells, memory CD8$^+$ T cells, NK cells, and NKT cells relative to the proliferation of one or more of these cells in individuals who have not been administered the composition;
   (ii) stimulates the proliferation of CD3+CD8+ T cells and/or CD3+CD4+ T cells up to five fold relative to the proliferation of one or more of these cells in individuals who have not been administered the composition;
   (iii) stimulates increased production of interferon gamma (IFNγ) relative to the production of IFNγ in individuals who have not been administered the composition; and/or
   (iv) prevents relapse of AML relative to the rate of relapse of AML in individuals who have not been administered the composition.

12. The method of claim 8, wherein the individual is a human.

13. The method of claim 8, wherein the recombinant leukemia cells are acute myelogenous leukemia cells.

14. The method of claim 8, wherein the individual is about 60 years of age or older.

15. The method of claim 8, wherein the composition is irradiated.

16. The method of claim 8, wherein the recombinant leukemia cells are created by transduction with a vector comprising the multicistronic nucleic acid molecule.

17. The method of claim 16, wherein the vector is a tri-cistronic vector.

18. The method of claim 8, wherein the method results in increased progression free survival of the individual relative to the rate of progression free survival in individuals with AML who have not been administered the vaccine.

19. A method of treating acute myelogenous leukemia (AML) in remission with persistent minimal residual disease comprising administering to a patient in need thereof an effective amount of a cell media composition according to claim 1.

* * * * *